(12) United States Patent
Phillips et al.

(10) Patent No.: US 10,085,730 B2
(45) Date of Patent: Oct. 2, 2018

(54) HEMOSTATIC DEVICE AND ITS METHODS OF USE

(71) Applicant: Phillips Medical, LLC, Jefferson City, MO (US)

(72) Inventors: Victor Matthew Phillips, Jefferson City, MO (US); William Robert Rebh, Jr., Shrewsbury, MA (US)

(73) Assignee: Phillips Medical, LLC, Jefferson City, MO (US)

( * ) Notice: Subject to any disclaimer, the term of this patent is extended or adjusted under 35 U.S.C. 154(b) by 579 days.

(21) Appl. No.: 14/708,943

(22) Filed: May 11, 2015

(65) Prior Publication Data
US 2015/0282791 A1    Oct. 8, 2015

Related U.S. Application Data

(63) Continuation-in-part of application No. 13/940,766, filed on Jul. 12, 2013, now Pat. No. 9,839,416.

(51) Int. Cl.
*A61B 17/50* (2006.01)
*A61D 1/00* (2006.01)
*A61B 17/00* (2006.01)

(52) U.S. Cl.
CPC .. *A61B 17/0057* (2013.01); *A61B 2017/0065* (2013.01); *A61B 2017/00371* (2013.01);
(Continued)

(58) Field of Classification Search
CPC .......... A61B 17/0057; A61B 17/00491; A61B 2017/00654; A61B 2017/00637;
(Continued)

(56) References Cited

U.S. PATENT DOCUMENTS

| 4,608,965 A | * | 9/1986 | Anspach, Jr. ...... A61B 17/0281 |
| | | | 600/101 |
| 4,738,658 A | | 4/1988 | Magro et al. |

(Continued)

FOREIGN PATENT DOCUMENTS

| WO | 0007505 A1 | 2/2000 |
| WO | 03047434 A1 | 6/2003 |

(Continued)

OTHER PUBLICATIONS

International Search Report and Written Opinion, dated Jan. 12, 2016, for co-pending International application No. PCT/US2015/040116 (16 pgs.).
(Continued)

*Primary Examiner* — Elizabeth Houston
*Assistant Examiner* — Mohamed Gabr
(74) *Attorney, Agent, or Firm* — Armstrong Teasdale LLP

(57) ABSTRACT

A hemostatic device for sealing a puncture of a vessel includes a first tube defining a first lumen, and a malecot coupled to the first tube. The malecot is selectively actuatable from a neutral configuration to a stopper configuration. The hemostatic device also includes a second tube circumscribing at least a portion of the first tube. The second tube at least partially defines a second lumen and a third lumen. The second tube includes a first opening in flow communication with the third lumen and positioned proximally relative to the malecot. The second tube is selectively orientable to at least partially expose a hemocoagulant agent retained in the second lumen.

8 Claims, 21 Drawing Sheets

(52) U.S. Cl.
CPC ............... *A61B 2017/00601* (2013.01); *A61B 2017/00659* (2013.01); *A61B 2017/00672* (2013.01); *A61B 2017/00884* (2013.01); *A61B 2017/00986* (2013.01)

(58) Field of Classification Search
CPC .. A61B 2017/00672; A61B 2017/0065; A61B 2017/0004; A61B 2017/00495; A61B 2017/00659; A61B 2017/22067; A61B 2017/00991; A61B 2090/062; A61F 2/06; A61F 13/26; A61M 25/0062; A61M 25/04; A61M 2025/0681; A61M 2025/1052; A61M 3/0279
See application file for complete search history.

(56) References Cited

U.S. PATENT DOCUMENTS

| | | |
|---|---|---|
| 4,850,960 A | 7/1989 | Grayzel |
| 4,890,612 A | 1/1990 | Kensey |
| 4,895,564 A | 1/1990 | Farrell |
| 4,929,246 A | 5/1990 | Sinofsky |
| 5,061,274 A | 10/1991 | Kensey |
| 5,108,421 A | 4/1992 | Fowler |
| 5,222,974 A | 6/1993 | Kensey et al. |
| 5,282,827 A | 2/1994 | Kensey et al. |
| 5,290,310 A | 3/1994 | Makower et al. |
| 5,306,254 A | 4/1994 | Nash et al. |
| 5,324,306 A | 6/1994 | Makower et al. |
| 5,326,350 A | 7/1994 | Li |
| RE34,866 E | 2/1995 | Kensey et al. |
| 5,391,183 A | 2/1995 | Janzen et al. |
| 5,411,520 A | 5/1995 | Nash et al. |
| 5,415,657 A | 5/1995 | Taymor-Luria |
| 5,431,639 A | 7/1995 | Shaw |
| 5,437,292 A | 8/1995 | Kipshidze et al. |
| 5,437,631 A | 8/1995 | Janzen |
| 5,441,517 A | 8/1995 | Kensey et al. |
| 5,443,481 A | 8/1995 | Lee |
| 5,486,195 A * | 1/1996 | Myers ............... A61B 17/0057 606/191 |
| 5,591,204 A | 1/1997 | Janzen et al. |
| 5,645,566 A | 7/1997 | Brenneman et al. |
| 5,653,730 A | 8/1997 | Hammerslag |
| 5,665,107 A | 9/1997 | Hammerslag |
| 5,676,689 A | 10/1997 | Kensey et al. |
| 5,707,393 A | 1/1998 | Kensey et al. |
| 5,716,375 A | 2/1998 | Fowler |
| 5,725,498 A | 3/1998 | Janzen et al. |
| 5,741,223 A | 4/1998 | Janzen et al. |
| 5,766,157 A | 6/1998 | Tilton, Jr. |
| 5,766,206 A | 6/1998 | Wijkamp et al. |
| 5,782,861 A | 7/1998 | Cragg et al. |
| 5,827,304 A | 10/1998 | Hart |
| 5,843,124 A | 12/1998 | Hammerslag |
| 5,868,762 A | 1/1999 | Cragg et al. |
| 5,935,147 A | 8/1999 | Kensey et al. |
| 5,951,583 A | 9/1999 | Jensen et al. |
| 5,984,950 A | 11/1999 | Cragg et al. |
| 6,045,570 A | 4/2000 | Epstein et al. |
| 6,056,768 A | 5/2000 | Cates et al. |
| 6,090,130 A | 7/2000 | Nash et al. |
| 6,190,360 B1 | 2/2001 | Iancea et al. |
| 6,254,571 B1 | 7/2001 | Hart |
| 6,296,657 B1 | 10/2001 | Brucker |
| 6,302,898 B1 | 10/2001 | Edwards et al. |
| 6,315,753 B1 | 11/2001 | Cragg et al. |
| 6,325,789 B1 | 12/2001 | Janzen et al. |
| 6,371,974 B1 | 4/2002 | Brenneman et al. |
| 6,371,975 B2 | 4/2002 | Cruise et al. |
| 6,500,152 B1 | 12/2002 | Illi |
| 6,527,734 B2 | 3/2003 | Cragg et al. |
| 6,544,236 B1 | 4/2003 | Cragg et al. |
| 6,547,806 B1 | 4/2003 | Ding |
| 6,610,026 B2 | 8/2003 | Cragg et al. |
| 6,743,248 B2 | 6/2004 | Edwards et al. |
| 6,818,008 B1 | 11/2004 | Cates et al. |
| 6,830,756 B2 | 12/2004 | Hnojewyj |
| 6,863,680 B2 | 3/2005 | Ashby |
| 6,866,669 B2 | 3/2005 | Buzzard et al. |
| 6,939,352 B2 | 9/2005 | Buzzard et al. |
| 6,984,219 B2 | 1/2006 | Ashby et al. |
| 7,029,489 B1 | 3/2006 | Ashby et al. |
| 7,037,322 B1 | 5/2006 | Sing et al. |
| 7,048,710 B1 | 5/2006 | Cragg et al. |
| 7,201,725 B1 | 4/2007 | Cragg et al. |
| 7,318,933 B2 | 1/2008 | Hnojewyj |
| 7,335,219 B1 | 2/2008 | Ashby et al. |
| 7,455,680 B1 | 11/2008 | Ashby et al. |
| 7,476,244 B2 | 1/2009 | Buzzard et al. |
| 7,611,479 B2 | 11/2009 | Cragg et al. |
| 7,625,352 B1 | 12/2009 | Ashby et al. |
| 7,776,062 B2 | 8/2010 | Besselink et al. |
| 8,088,145 B2 | 1/2012 | Zhu et al. |
| 8,382,786 B2 | 2/2013 | Besselink et al. |
| 8,617,253 B2 | 12/2013 | Zhu et al. |
| 9,179,902 B2 | 11/2015 | Zhu et al. |
| 9,554,789 B2 | 1/2017 | Overes et al. |
| 2001/0018598 A1 | 8/2001 | Cruise et al. |
| 2003/0088271 A1 | 5/2003 | Cragg et al. |
| 2003/0100921 A1 | 5/2003 | Addis et al. |
| 2003/0191516 A1 | 10/2003 | Weldon et al. |
| 2004/0019328 A1 | 1/2004 | Sing et al. |
| 2004/0098024 A1 | 5/2004 | Dieck et al. |
| 2004/0102730 A1 | 5/2004 | Davis et al. |
| 2006/0100664 A1 | 5/2006 | Pai et al. |
| 2006/0276838 A1 | 12/2006 | Wensel et al. |
| 2007/0038245 A1 | 2/2007 | Morris et al. |
| 2007/0123816 A1 | 5/2007 | Zhu et al. |
| 2008/0038313 A1 | 2/2008 | Addis et al. |
| 2008/0046005 A1 | 2/2008 | Lenker et al. |
| 2008/0071310 A1 | 3/2008 | Hoffman et al. |
| 2008/0082122 A1 | 4/2008 | Khosravi et al. |
| 2008/0161849 A1 | 7/2008 | Cates et al. |
| 2009/0088793 A1 | 4/2009 | Bagaoisan et al. |
| 2009/0143808 A1 | 6/2009 | Houser |
| 2009/0171282 A1 * | 7/2009 | Pipenhagen ....... A61B 17/0057 604/103.01 |
| 2009/0312748 A1 | 12/2009 | Johnson et al. |
| 2010/0211000 A1 | 8/2010 | Killion et al. |
| 2011/0137338 A1 | 6/2011 | Phillips |
| 2012/0265243 A1 | 10/2012 | Phillips |
| 2013/0060279 A1 * | 3/2013 | Yassinzadeh ...... A61B 17/0057 606/213 |
| 2015/0018871 A1 | 1/2015 | Phillips et al. |

FOREIGN PATENT DOCUMENTS

| | | |
|---|---|---|
| WO | 2006093970 A1 | 9/2006 |
| WO | 2008079810 A2 | 7/2008 |
| WO | 2013033477 A1 | 3/2013 |

OTHER PUBLICATIONS

EP Extended Search Report, dated Mar. 1, 2017, for European patent application No. EP 14822893.5 (8 pgs).
International Search Report and Written Opinion of PCT/US2011/032490; dated Jun. 29, 2011; 10 pages.
International Search Report and Written Opinion, dated Nov. 12, 2014, for International application No. PCT/US14/46260 (10 pgs.).

\* cited by examiner

HEMOSTATIC DEVICE AND ITS METHODS OF USE

CROSS-REFERENCE TO RELATED APPLICATIONS

This application is a continuation-in-part of U.S. patent application Ser. No. 13/940,766, filed Jul. 12, 2013, entitled "HEMOSTATIC DEVICE AND ITS METHODS OF USE," the disclosure of which is hereby incorporated herein by reference in its entirety.

BACKGROUND

The subject matter described herein relates generally to medical devices and, more particularly, to a hemostatic device configured to seal a puncture of a vessel.

Catheter introducers are known to provide access to an artery for at least some medical procedures including, without limitation, cardiac catheterizations and peripheral endovascular procedures. After conducting such medical procedures, the catheter introducer is removed from the access site, leaving an arterial opening. At least some body fluids including, without limitation, blood are discharged from the arterial opening. Excess blood loss may endanger and/or traumatize the patient. One known method of controlling blood loss is through direct manual pressure over the arterial opening.

BRIEF SUMMARY

In one aspect, a method for sealing a puncture of a vessel using a hemostatic device is provided. The hemostatic device includes a first tube defining a first lumen, a malecot coupled to the first tube, and a second tube circumscribing at least a portion of the first tube and at least partially defining a second lumen and a third lumen. The method includes retaining a hemocoagulant agent in the second lumen, and advancing a distal end of the hemostatic device into the vessel until a fluid is channeled through a first opening of the second tube into the third lumen. The first opening is positioned proximally relative to the malecot. The method also includes transitioning the malecot from a neutral configuration to a stopper configuration, withdrawing the hemostatic device until the malecot abuts an interior surface of vessel wall, and selectively orienting the second tube such that the hemocoagulant agent is at least partially exposed.

In another aspect, a hemostatic device for sealing a puncture of a vessel is provided. The hemostatic device includes a first tube defining a first lumen, and a malecot coupled to the first tube. The malecot is selectively actuatable from a neutral configuration to a stopper configuration. The hemostatic device also includes a second tube circumscribing at least a portion of the first tube. The second tube at least partially defines a second lumen and a third lumen. The second tube includes a first opening in flow communication with the third lumen and positioned proximally relative to the malecot. The second tube is selectively orientable to at least partially expose a hemocoagulant agent retained in the second lumen.

In yet another aspect, a hemostatic device for sealing a puncture of a vessel is provided. The hemostatic device includes a first tube defining a first lumen, a malecot coupled to the first tube, and a second tube circumscribing at least a portion of the first tube. The second tube at least partially defines a second lumen and a third lumen. The second tube includes a first opening in flow communication with the third lumen and positioned proximally relative to the malecot. The second tube is selectively orientable to at least partially expose a hemocoagulant agent retained in the second lumen. The hemostatic device also includes a plug actuator configured to transition the malecot from a neutral configuration to a stopper configuration.

The features, functions, and advantages described herein may be achieved independently in various embodiments of the present disclosure or may be combined in yet other embodiments, further details of which may be seen with reference to the following description and drawings.

DETAILED DESCRIPTION

The methods and apparatus described herein relate to medical devices and, more particularly, to a hemostatic device for use in sealing a puncture of a vessel. The hemostatic device described herein facilitates sealing an opening of a blood vessel. More particularly, in at least one embodiment, the hemostatic device includes a first tube defining a first lumen, and a second tube circumscribing at least a portion of the first tube and at least partially defining a second lumen configured to retain a hemocoagulant agent therein. A malecot is coupled to the first tube. The second tube is movable with respect to the first tube, such that the hemocoagulant agent is at least substantially retained within the second lumen when the second tube is oriented in a first position, and the hemocoagulant agent is at least partially exposed when the second tube is oriented in a second position. The hemocoagulant agent is discharged from the second lumen and seals the opening to reduce a time required for hemostasis and/or ambulation. The malecot facilitates positioning the second tube outside the lumen of the vessel, and adjacent to the vessel wall, prior to the release of hemocoagulant agent, and substantially seals the vessel wall from penetration by the hemocoagulant agent at the access site.

As used herein, an element or step recited in the singular and preceded with the word "a" or "an" should be understood as not excluding plural said elements or steps, unless such exclusion is explicitly stated. Further, references to an "embodiment" or an "implementation" are not intended to be interpreted as excluding the existence of additional embodiments or implementations that also incorporate the recited features. Moreover, unless explicitly stated to the contrary, embodiments or implementations "comprising," "including," or "having" an element or a plurality of elements having a particular property may include additional such elements not having that property.

Figure 1:
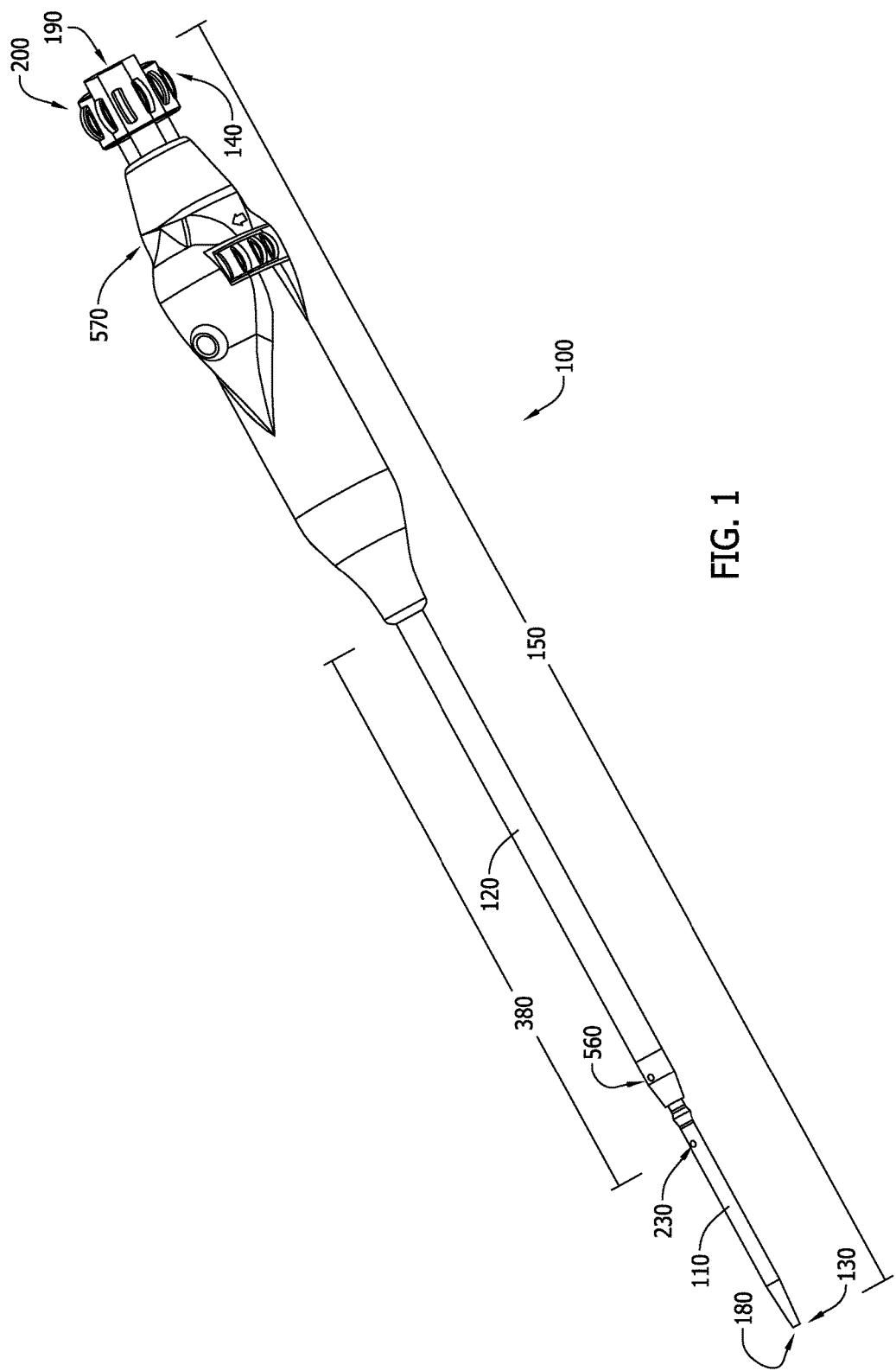
FIG. 1 is a perspective view of an exemplary hemostatic device.

FIG. 1 is a perspective view of an exemplary hemostatic device 100 for sealing a puncture of a vessel (not shown). In the exemplary embodiment, hemostatic device 100 includes a first or inner tube 110 and a second or outer tube 120. In the exemplary embodiment, hemostatic device 100 has a distal end 130, a proximal end 140, and a length 150. In the exemplary embodiment, length 150 is at least approximately 5 inches (in.). More particularly, length 150 is between approximately 8 in. and approximately 12 in. Even more particularly, length 150 is approximately 10.147 in. Alternatively, hemostatic device 100 may have any length that enables the methods and systems to function as described herein. In the exemplary embodiment, a distal end of inner tube 110 is tapered to facilitate traversing through subcutaneous tissue and into a lumen of the vessel.

Figure 2:
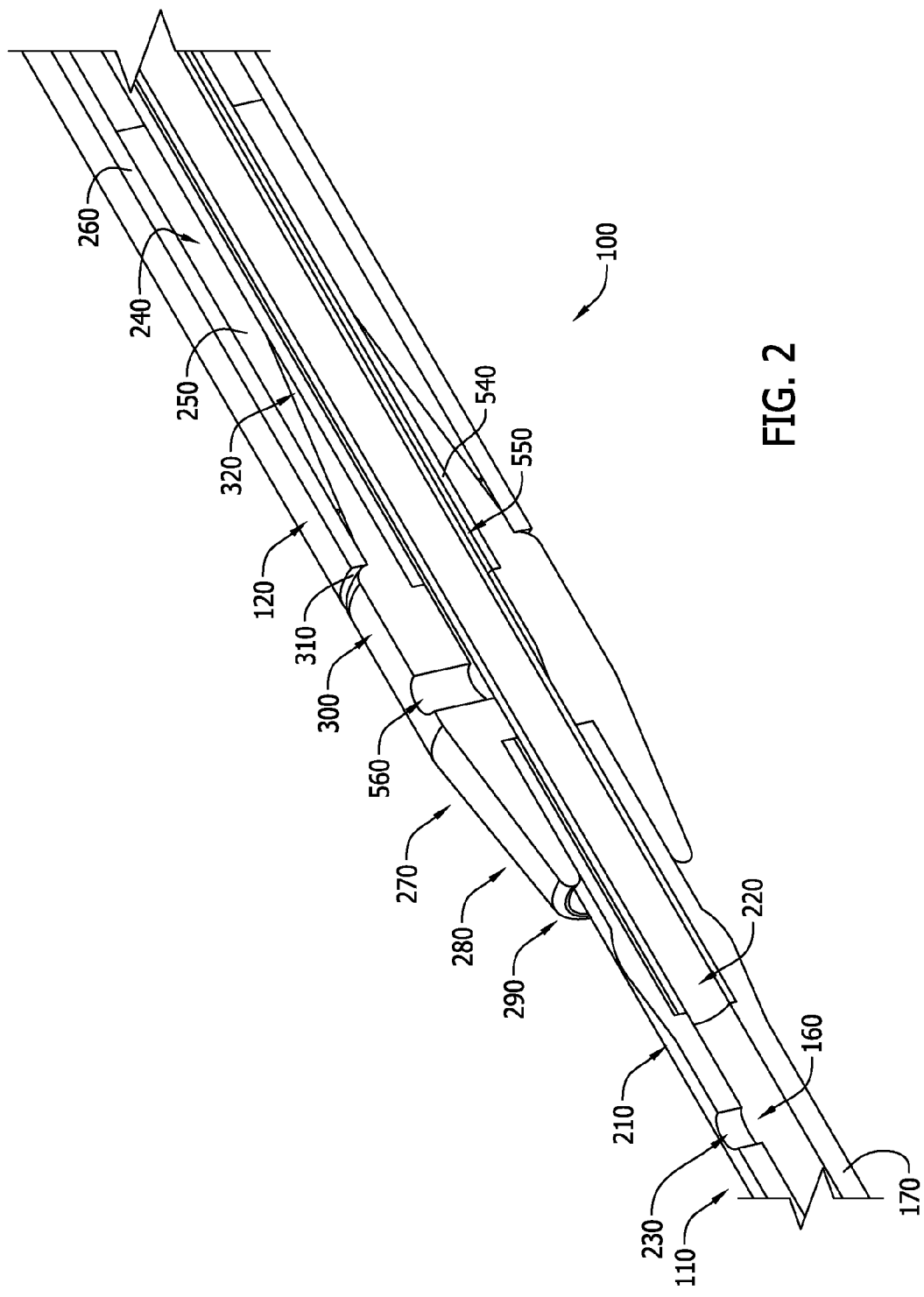
FIG. 2 is a cross-sectional view of a distal portion of the hemostatic device shown in FIG. 1 in a closed configuration.
Figure 3:
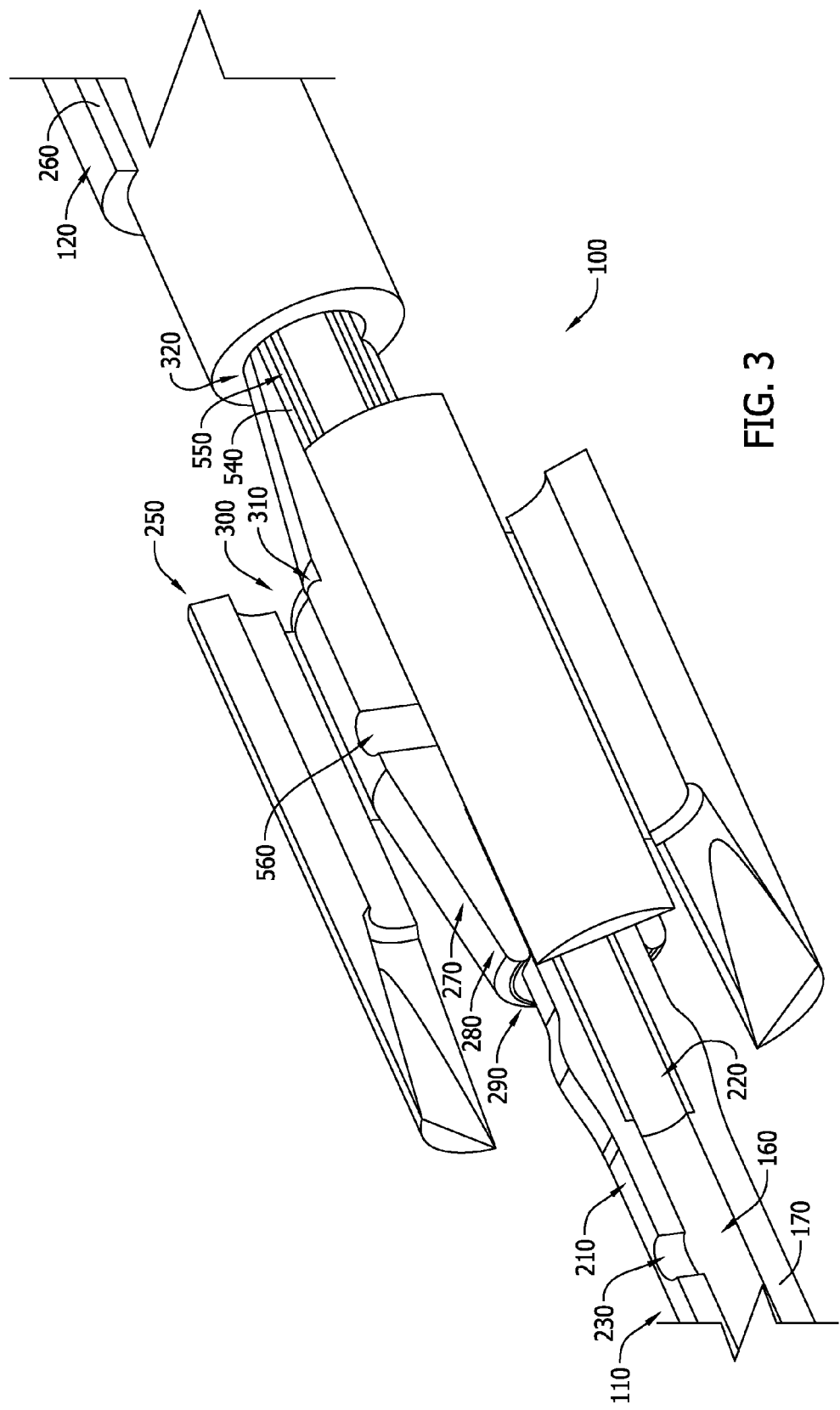
FIG. 3 is a cross-sectional view of the distal portion shown in FIG. 2 in a deployed configuration.

FIG. 2 is a cross-sectional view of a first portion of hemostatic device 100 in a closed configuration, and FIG. 3 is a cross-sectional view of the first portion in a deployed configuration. In the exemplary embodiment, inner tube 110 includes a sidewall 170 that defines a first or inner lumen 160 configured to channel blood or, more broadly, a fluid therethrough. In the exemplary embodiment, sidewall 170 includes a first opening 180 (shown in FIG. 1) at a distal end of inner lumen 160, and a second opening 190 (shown in FIG. 1) at a proximal end of inner lumen 160. In the exemplary embodiment, first opening 180 is sized to receive a guidewire (not shown), and second opening 190 is sized to channel the fluid through inner lumen 160 about the guidewire. First opening 180 and/or second opening 190 may have any size, shape, and/or configuration that enables inner tube 110 to function as described herein.

In the exemplary embodiment, a valve 200 (shown in FIG. 1) proximate to second opening 190 is selectively movable between an open configuration and a closed configuration. More particularly, valve 200 is actuatable towards the closed configuration to selectively restrict access to second opening 190 and/or inner lumen 160. That is, in the exemplary embodiment, valve 200 enables second opening 190 to be at least partially closed such that a flow of the fluid through inner lumen 160 is decreased. Moreover, in the exemplary embodiment, valve 200 is actuatable towards the open configuration to selectively provide access to second opening 190 and/or inner lumen 160. That is, in the exemplary embodiment, valve 200 enables second opening 190 to be at least partially opened such that a flow of the fluid through inner lumen 160 is increased.

In the exemplary embodiment, inner tube 110 includes a distal portion 210 and a proximal portion 220 coupled to distal portion 210 by an interference fit. Alternatively, inner tube 110 may include any number of portions, and/or the portions may be coupled in any configuration and/or using any mechanism that enables inner tube 110 to function as described herein. In the exemplary embodiment, outer tube 120 houses proximal portion 220 of inner tube 110, and distal portion 210 is generally exposed, such that outer tube 120 does not house distal portion 210 of inner tube 110. In the exemplary embodiment, distal portion 210 includes a side opening 230 extending through sidewall 170 that is in fluid communication with inner lumen 160 such that fluid may enter inner lumen 160 through side opening 230.

In the exemplary embodiment, outer tube 120 includes a sidewall 260 that at least partially defines a second or outer lumen 240 (shown in FIG. 2) configured to retain a hemocoagulant agent 250 therein. In one implementation, hemocoagulant agent 250 is an FDA-approved hydrogel polymer or collagen patch. Alternatively, hemocoagulant agent 250 may be any substance and/or composition that enables outer tube 120 to function as described herein.

In the exemplary embodiment, outer tube 120 houses at least a portion of inner tube 110. In the exemplary embodiment, outer tube 120 is translatable or longitudinally movable with respect to inner tube 110, such that hemocoagulant agent 250 is at least substantially retained within outer lumen 240 when outer tube 120 is in a first or closed position, and is at least partially exposed to the environment when outer tube 120 is in a second or open position. Outer tube 120 is slidable in the distal direction towards the closed position to substantially retain hemocoagulant agent 250 within outer lumen 240, and is slidable in the proximal direction towards the open position to expose hemocoagulant agent 250 to the environment. Alternatively, inner tube 110 and outer tube 120 may move in any direction that enables hemostatic device 100 to function as described herein.

In the exemplary embodiment, hemostatic device 100 includes a plug 270 that at least partially circumscribes inner tube 110. In the exemplary embodiment, plug 270 includes a distal portion 280 having a distal apex 290 oriented towards the distal end of hemostatic device 100, and a proximal portion 300 having a step 310 and a proximal apex 320 oriented towards the proximal end of hemostatic device 100. In the exemplary embodiment, plug 270 is positioned with respect to inner tube 110, such that plug 270 and/or a distal end of outer tube 120 are positionable outside and substantially adjacent an access site and/or a vessel when inner tube side opening 230 is within the lumen of the vessel.

In the exemplary embodiment, plug distal portion 280 is substantially cone-shaped to facilitate traversing plug 270 through subcutaneous tissue, and plug proximal portion 300 is substantially cone-shaped to facilitate channeling or directing hemocoagulant agent 250 radially outward from hemostatic device 100. In the exemplary embodiment, plug proximal portion 300 is oriented and/or configured to channel or direct at least some of hemocoagulant agent 250 away from inner tube 110 and/or a center axis of hemostatic device 100 to facilitate reducing a coagulation of hemocoagulant agent 250 within outer lumen 240.

In the exemplary embodiment, step 310 is configured to interface and/or receive a distal end of outer tube 120, such that hemocoagulant agent 250 is at least substantially retained within outer lumen 240 when hemostatic device 100 is in a closed configuration. Step 310 enables outer tube 120 to be sealingly coupled to plug 270, such that hemocoagulant agent 250 is at least substantially retained within outer lumen 240. In the exemplary embodiment, plug 270 is fabricated at least partially from a soft and/or pliable material that enables a seal to be provided at the plug-outer tube interface, the vessel, and/or the access site. For example, plug 270 may be fabricated from, without limitation, rubber and/or a rubber-like material. Alternatively, plug 270 may have any configuration that enables plug 270 to function as described herein.

Figure 4:
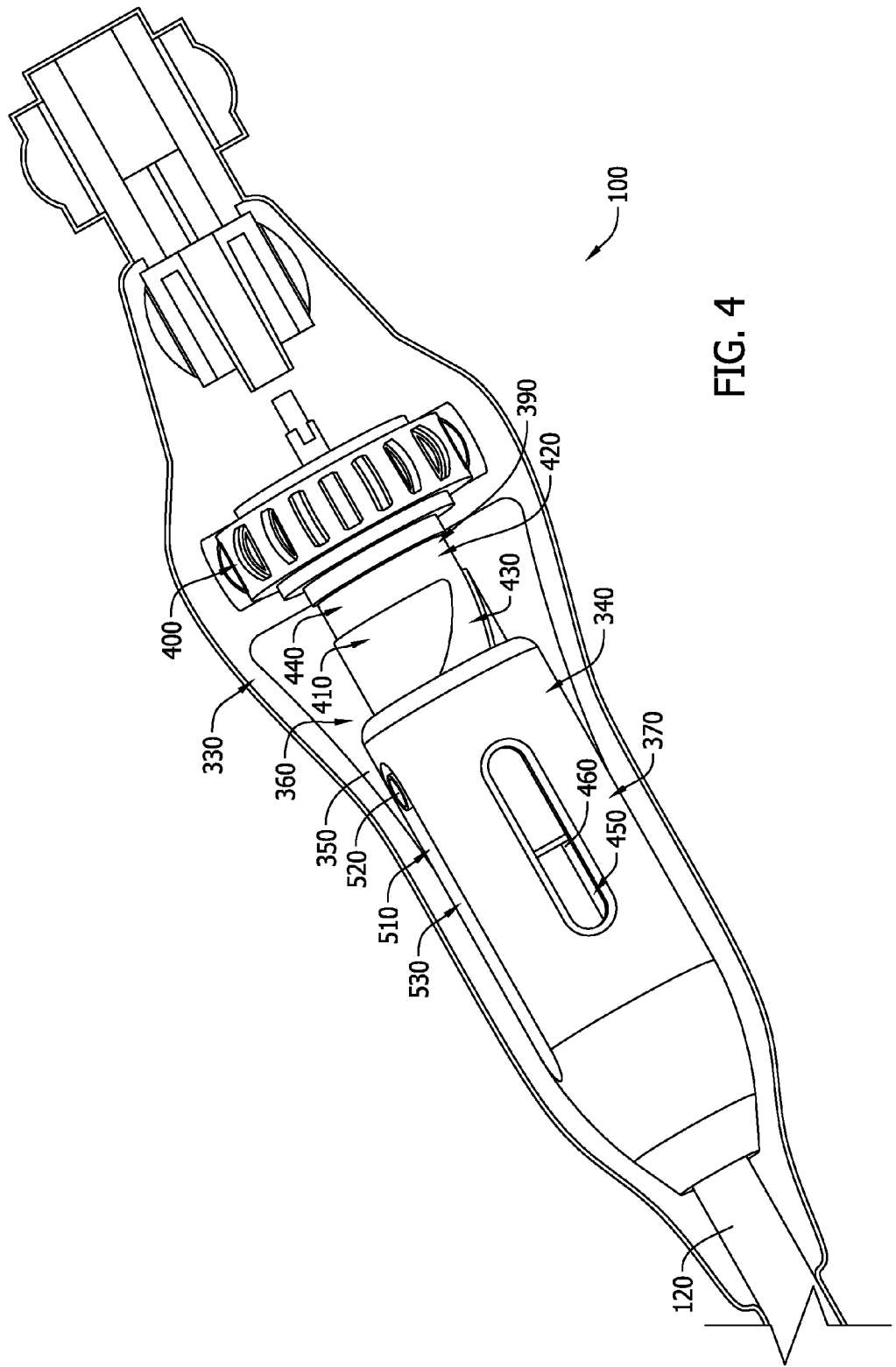
FIG. 4 is a partial cross-sectional view of a proximal portion of the hemostatic device shown in FIG. 1 in a closed configuration.
Figure 5:
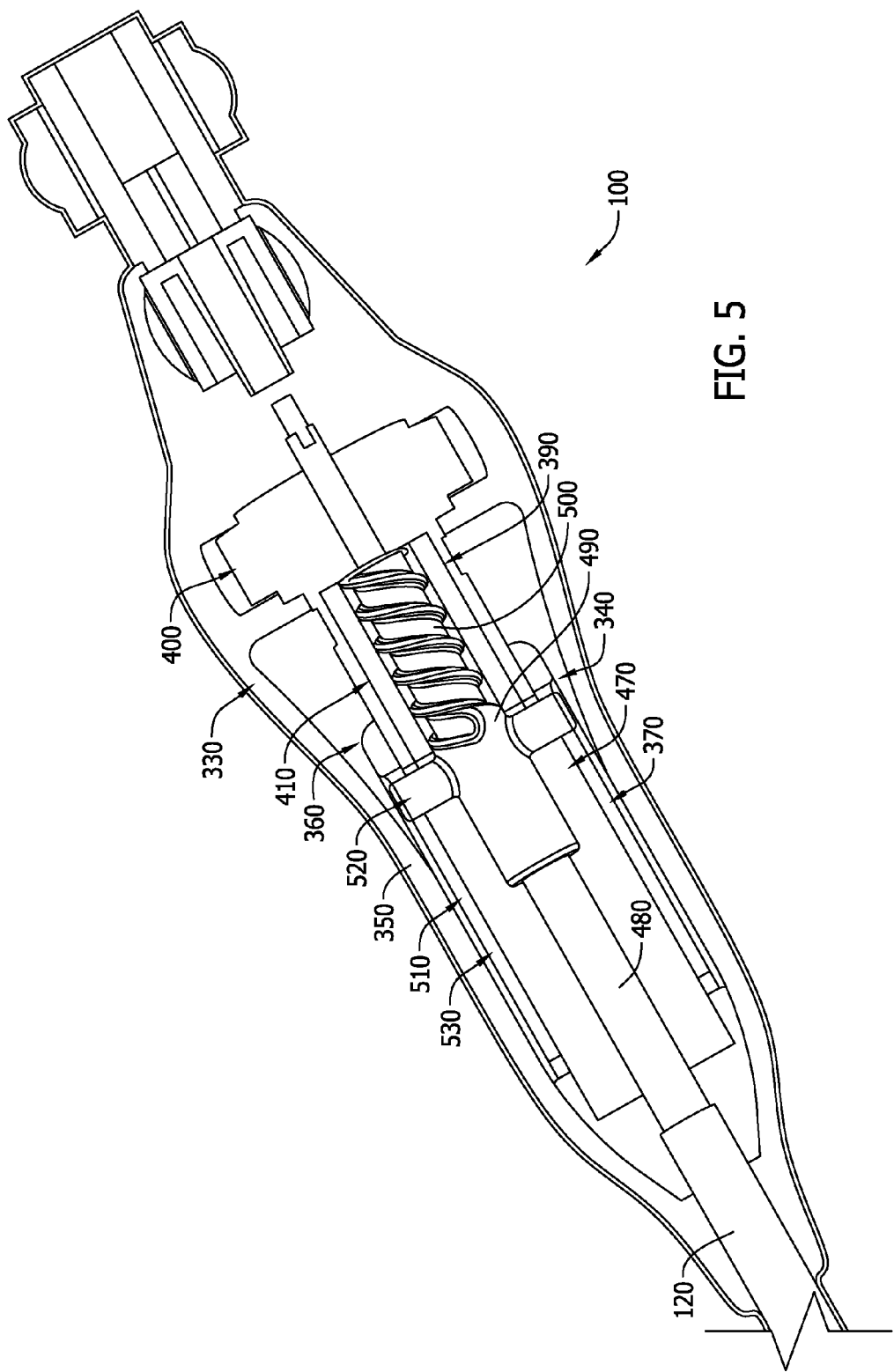
FIG. 5 is a cross-sectional view of the proximal portion shown in FIG. 4.
Figure 6:
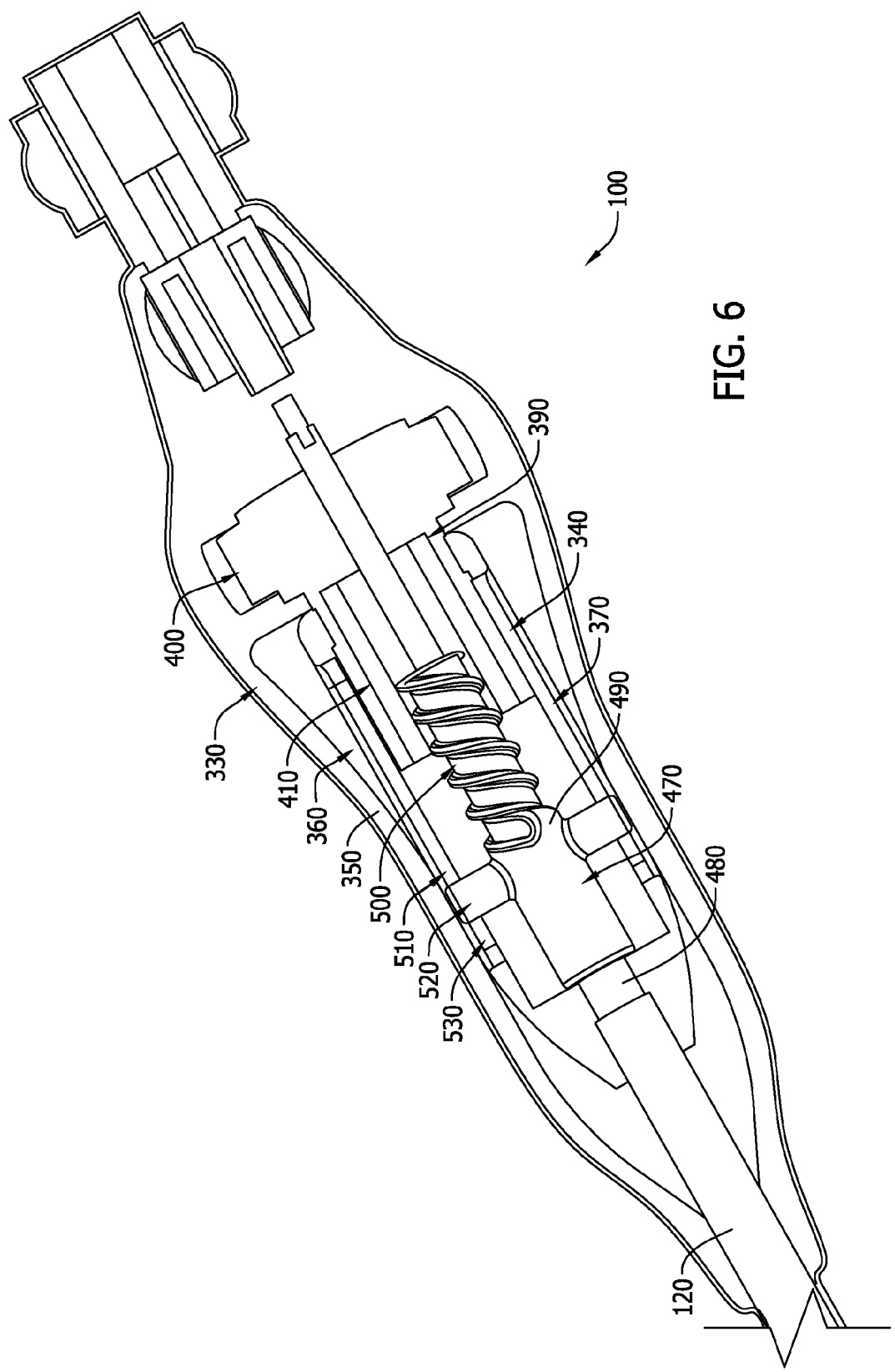
FIG. 6 is a cross-sectional view of the proximal portion shown in FIG. 4 in a deployed configuration.

FIGS. 4 and 5 are cross-sectional views of a second portion of hemostatic device 100 in a closed configuration, and FIG. 6 is a cross-sectional view of the second portion in a deployed configuration. In the exemplary embodiment, hemostatic device 100 includes a housing 330 and an actuating mechanism 340 positioned within housing 330. More specifically, housing 330 includes a sidewall 350 that defines a cavity 360, and actuating mechanism 340 includes a first or an outer tube carrier 370 that is movable within cavity 360 between a distal end of cavity 360 and a proximal end of cavity 360. In the exemplary embodiment, outer tube carrier 370 is coupled to outer tube 120 such that outer tube 120 moves between the closed position and the open position as outer tube carrier 370 is moved between the distal end of cavity 360 and the proximal end of cavity 360, respectively. Alternatively, outer tube 120 may be moved towards the open position and/or the closed position using any mechanism that enables outer tube 120 to function as described herein.

In the exemplary embodiment, a distance 380 (shown in FIG. 1) between side opening 230 and a distal end of housing 330 is at least approximately 2 in. More particularly, distance 380 is between approximately 3 in. and approximately 6 in. Even more particularly, distance 380 is approximately 4.2 in. Alternatively, distance 380 may be any length that enables the methods and systems to function as described herein. In the exemplary embodiment, distance 380 remains substantially constant as at least a portion of outer tube 120 is selectively retracted into and/or extended from housing 330 when outer tube 120 is moved between the closed position and the open position.

In the exemplary embodiment, hemostatic device 100 includes a rotating mechanism 390 coupled to outer tube carrier 370. In the exemplary embodiment, rotating mechanism 390 is configured to move outer tube carrier 370 towards the distal end of cavity 360 as rotating mechanism 390 is rotated in a first direction (e.g., a counterclockwise direction when looking from proximal end 140 towards distal end 130) and move outer tube carrier 370 towards the proximal end of cavity 360 as rotating mechanism 390 is rotated in a second direction (e.g., a clockwise direction when looking from proximal end 140 towards distal end 130). Rotating mechanism 390 is configured to convert rotational movement into axial movement. In the exemplary embodiment, rotating mechanism 390 includes a wheel 400 and a body 410 extending from wheel 400 and at least partially positioned within outer tube carrier 370. In the exemplary embodiment, wheel 400 has a diameter that is greater than and/or equal to a width of housing 330.

In the exemplary embodiment, a peg (not shown) extending from an inner surface of outer tube carrier 370 is retained in a groove 420 (shown in FIG. 4) defined in an outer surface of body 410. In the exemplary embodiment, groove 420 includes a first segment 430 (shown in FIG. 4) that extends helically about a central axis of body 410 and a second segment 440 (shown in FIG. 4) that at least partially circumscribes body 410. In the exemplary embodiment, outer tube carrier 370 longitudinally moves with respect to rotating mechanism 390 between the distal end of cavity 360 and the proximal end of cavity 360 as wheel 400 is rotated when the peg is within first segment 430. Moreover, in the exemplary embodiment, outer tube carrier 370 is substantially longitudinally stationary with respect to rotating mechanism 390 as wheel 400 is rotated when the peg is within second segment 440. Alternatively, outer tube carrier 370 may be moved between the distal end of cavity 360 and the proximal end of cavity 360 using any mechanism that enables outer tube 120 to function as described herein. In at least some implementations, second segment 440 fully circumscribes body 410 to enable wheel 400 to be continuously rotated when the peg is within second segment 440. In at least some implementations, outer tube carrier 370 is at the proximal end of cavity 360 when the peg is within second segment 440.

In the exemplary embodiment, hemostatic device 100 includes a first retaining mechanism 450 (shown in FIG. 4) that facilitates preventing outer tube carrier 370 from rotating with respect to housing 330 as wheel 400 is rotated in the first direction and/or in the second direction. In the exemplary embodiment, retaining mechanism 450 includes a peg (not shown) extending from an inner surface of housing 330, and a slot 460 (shown in FIG. 4) defined in an outer surface of outer tube carrier 370 sized to retain the peg. In the exemplary embodiment, slot 460 extends substantially longitudinally along the outer surface of outer tube carrier 370, such that outer tube carrier 370 is longitudinally movable, while substantially not rotating, with respect to housing 330 as the peg is moved between a distal end of slot 460 and a proximal end of slot 460. Alternatively, outer tube 120 may be moved and/or restricted from movement using any mechanism that enables outer tube 120 to function as described herein.

In the exemplary embodiment, hemostatic device 100 includes a plunging mechanism 470 (shown in FIGS. 5 and 6) including a plunger 480 (shown in FIGS. 2, 3, 5, and 6) at least partially positioned within outer lumen 240 (shown in FIGS. 2 and 3), and a second or plunger carrier 490 (shown in FIGS. 5 and 6) movable within a cavity defined by outer tube carrier 370 and/or a cavity defined by rotating mechanism body 410 to facilitate discharging hemocoagulant agent 250.

In the exemplary embodiment, a peg (not shown) extending from an inner surface of rotating mechanism body 410 is retained in a groove 500 (shown in FIGS. 5 and 6) defined in an outer surface of plunger carrier 490. In the exemplary embodiment, groove 500 extends helically about a central axis of plunger carrier 490 in a direction that is opposite the direction associated with groove 420. In the exemplary embodiment, plunger 480 is longitudinally movable, with respect to outer tube 120, in a direction that is opposite the direction outer tube carrier 370 moves with respect to housing 330 as wheel 400 is rotated. For example, in the exemplary embodiment, wheel 400 is selectively rotatable in the first direction to simultaneously move outer tube 120 towards the closed position and plunger 480 towards a retracted or proximal position, or move outer tube 120 towards the open position and plunger 480 towards a dispensing or distal position. Groove 420 extends at a first angle with respect to the longitudinal axis, and groove 500 extends at a second angle that is different from the first angle. The first angle and/or the second angle are predefined, such that outer tube 120 is configured to move a first distance with each rotation of wheel 400, and plunger 480 is configured to move a second distance with each rotation of wheel 400 that is less than the first distance. Alternatively, outer tube 120 and/or plunger 480 may be moved using any mechanism that enables hemostatic device 100 to function as described herein.

In the exemplary embodiment, hemostatic device 100 includes a second retaining mechanism 510 that facilitates preventing plunger carrier 490 from rotating with respect to outer tube carrier 370 as wheel 400 is rotated. In the exemplary embodiment, retaining mechanism 510 includes a peg 520 (shown in FIGS. 5 and 6) extending from an outer surface of plunger carrier 490, and a slot 530 (shown in FIG. 4) defined in an inner surface of outer tube carrier 370 sized to retain peg 520. In the exemplary embodiment, slot 530 extends substantially longitudinally along the inner surface of outer tube carrier 370, such that plunging mechanism 470 is longitudinally movable, while substantially not rotating, with respect to outer tube carrier 370 as peg 520 is moved between a distal end of slot 530 and a proximal end of slot 530. Alternatively, plunging mechanism 470 may be moved and/or restricted from movement using any mechanism that enables plunging mechanism 470 to function as described herein.

In the exemplary embodiment, hemostatic device 100 includes a third or intermediate tube 540 (shown in FIGS. 2 and 3) positioned radially between inner tube 110 and outer tube 120. More specifically, intermediate tube 540 is positioned such that outer lumen 240 is defined between intermediate tube 540 and outer tube 120, and a third or intermediate lumen 550 (shown in FIGS. 2 and 3) configured to channel blood or, more broadly, a fluid therethrough is defined between intermediate tube 540 and inner tube 110. In the exemplary embodiment, intermediate lumen 550 is in fluid communication with a first opening 560 (shown in FIGS. 1-3) extending through plug 270 and a second opening 570 (shown in FIG. 1) extending through housing 330 such that fluid may enter intermediate lumen 550 through first opening 560 and is dischargeable through second opening 570.

Figure 7:
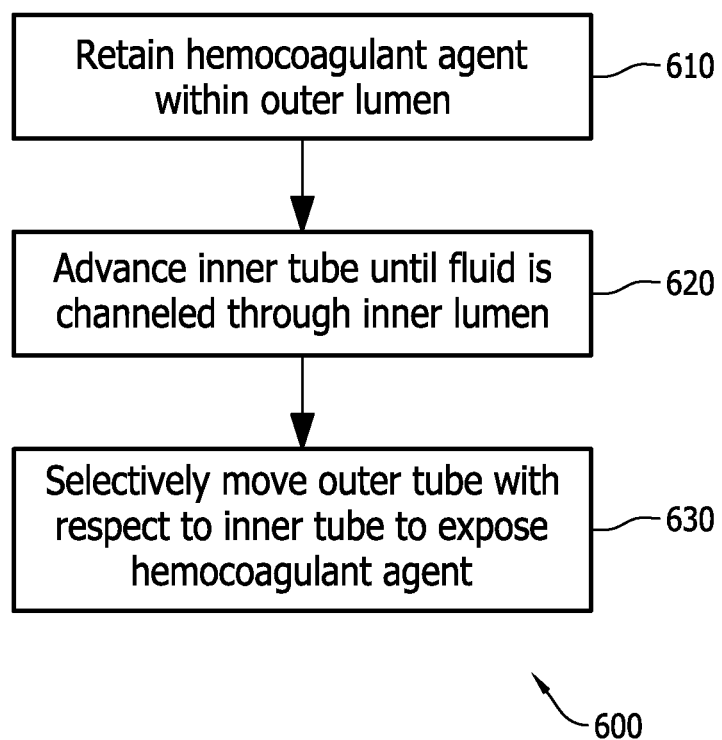
FIG. 7 is a flow chart illustrating an exemplary method of using the hemostatic device shown in FIG. 1.

FIG. 7 is a flow chart illustrating an exemplary method 600 of using hemostatic device 100 to seal a puncture of an artery or vessel with a hydrogel polymer or collagen patch hemocoagulant agent 250. In at least some implementations, hemocoagulant agent 250 is preloaded into hemostatic device 100, such that hemocoagulant agent is retained 610 within outer lumen 240. Alternatively, hemocoagulant agent 250 is loaded into hemostatic device 100, such that hemocoagulant agent is retained 610 within outer lumen 240, by selectively rotating wheel 400 and/or substantially enveloping or circumscribing hemocoagulant agent 250 about inner tube 110.

During operation, inner tube 110 is aligned such that a guidewire (not shown) extends through first opening 180 and second opening 190, and inner tube 110 is advanced 620 along the guidewire through subcutaneous tissue until blood is channeled through inner lumen 160 and/or discharged from second opening 190. In the exemplary embodiment, the blood discharge (i.e., reflux) from second opening 190 is a visual indication that inner tube side opening 230 is positioned within the vessel. Moreover, plug 270 provides a tactile indication (e.g., resistance) that plug 270 is positioned outside and substantially adjacent the vessel and/or inner tube side opening 230 is positioned within the vessel.

In the exemplary embodiment, valve 200 is moved towards the closed configuration to restrict access to second opening 190 and/or facilitate reducing blood flow through inner lumen 160. In at least some implementations, hemostatic device 100 is advanced along the guidewire too far through subcutaneous tissue. In such an implementation, the blood enters plug opening 560, is channeled through intermediate lumen 550, and/or is discharged from housing opening 570. In such an implementation, the blood discharge from housing opening 570 is a visual indication that hemostatic device 100 is advanced too far through subcutaneous tissue and/or should be at least partially withdrawn from the subcutaneous tissue until blood does not discharge from housing opening 570.

In the exemplary embodiment, wheel 400 is selectively rotated in the second direction to move hemostatic device 100 towards the deployed configuration and, thus, move 630 outer tube 120 towards the open position. Accordingly, in the exemplary embodiment, hemocoagulant agent 250 is at least partially exposed to the environment. As wheel 400 is selectively rotated in the second direction, plunger carrier 490 and, thus, plunger 480 is moved in the distal direction, such that hemocoagulant agent 250 is pushed at least partially in the distal direction towards plug 270. In at least some implementations, outer tube 120 is moved 630 towards the open position and plunger 480 is moved towards the distal direction simultaneously. In the exemplary embodiment, plug proximal portion 300 channels or directs at least some of hemocoagulant agent 250 radially outward and/or away from a center axis of hemostatic device 100.

Figure 8:
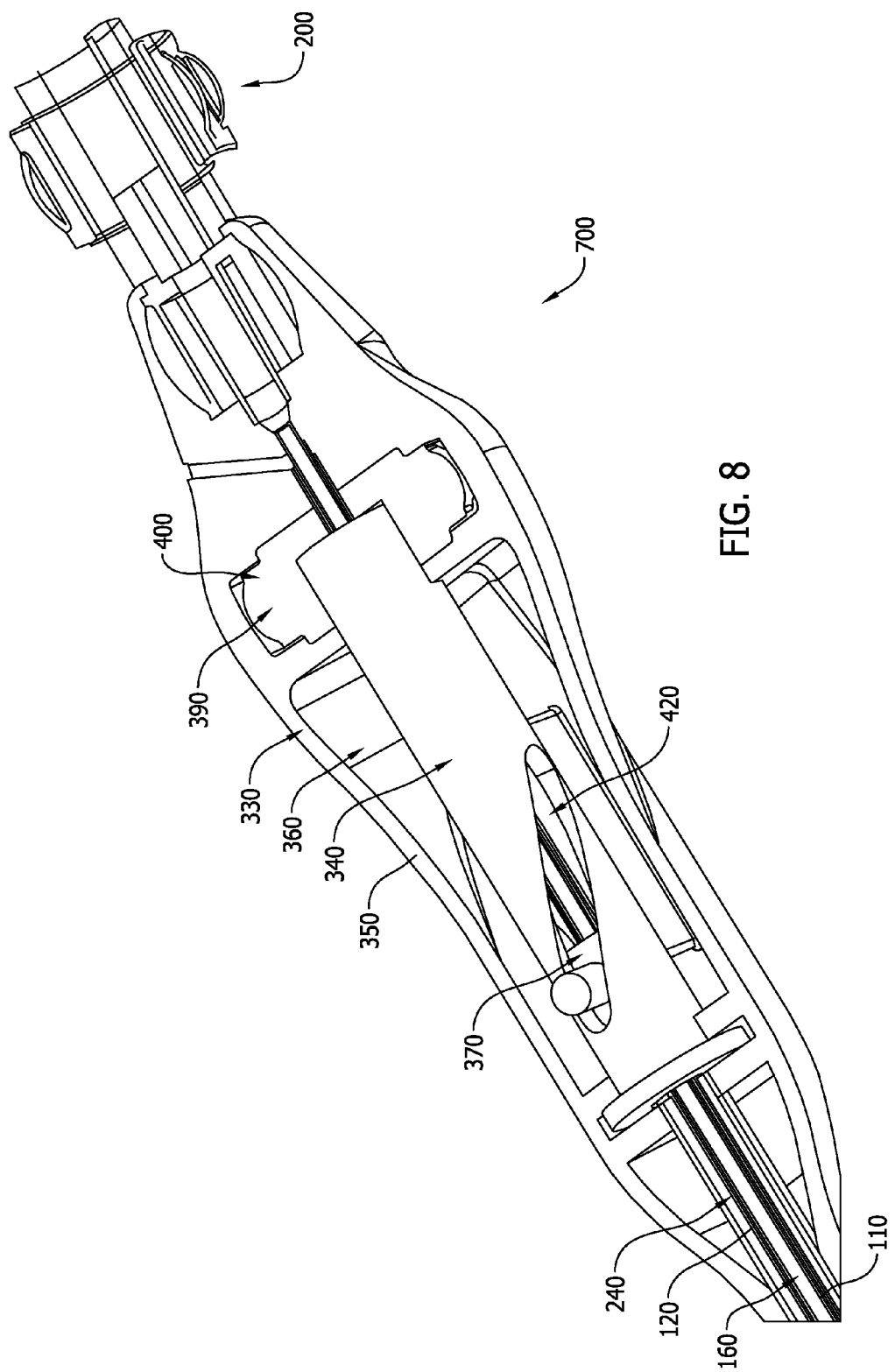
FIG. 8 is a partial cross-sectional view of another exemplary hemostatic device.

FIG. 8 is a partial cross-sectional view of another exemplary hemostatic device 700 for sealing a puncture of a vessel (not shown). Hemostatic device 700 is similar to hemostatic device 100 and, in the absence of a contrary representation, the same reference numbers identify the same or similar elements.

Figure 9:
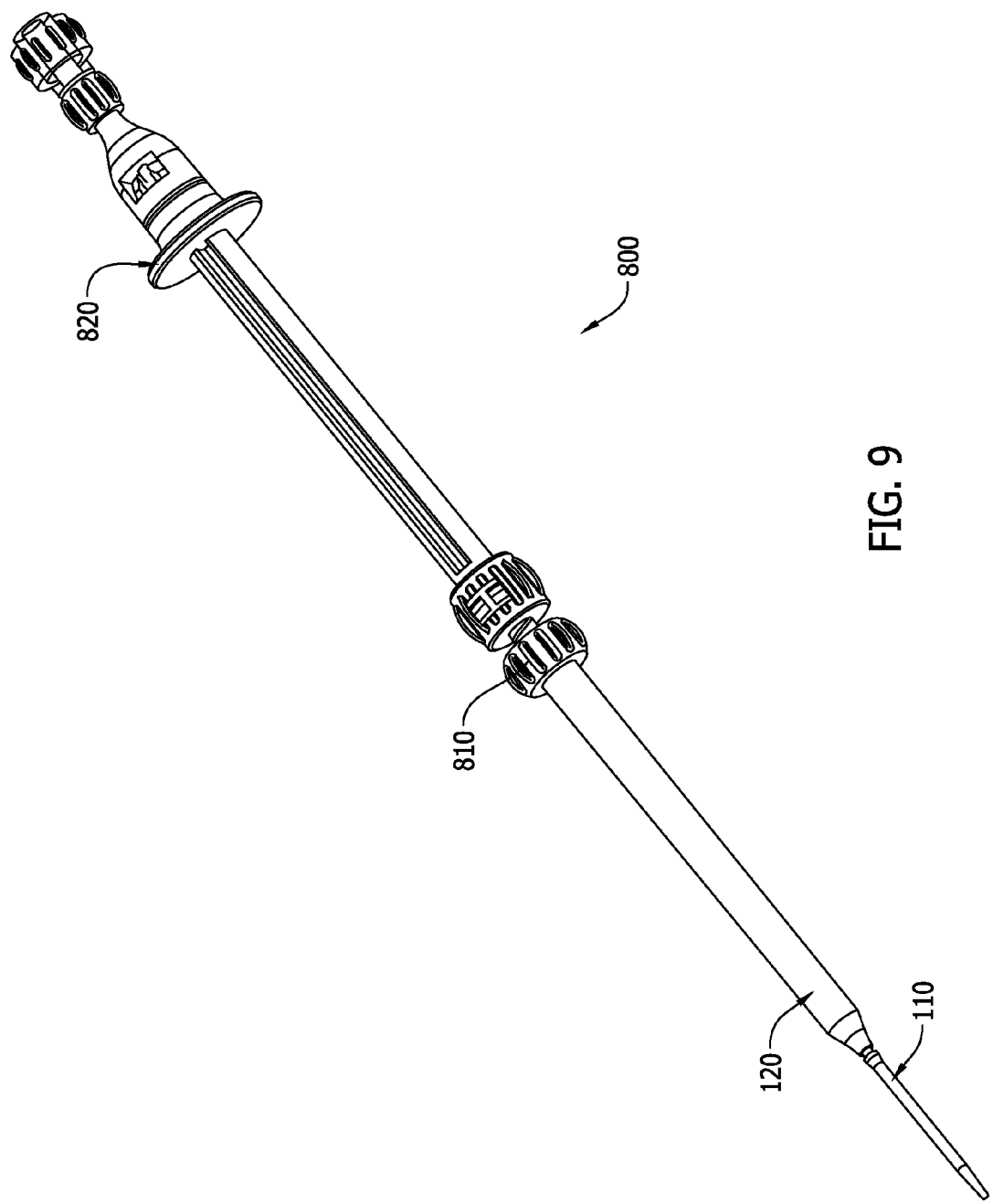
FIG. 9 is a perspective view of yet another exemplary hemostatic device in a closed configuration.
Figure 10:
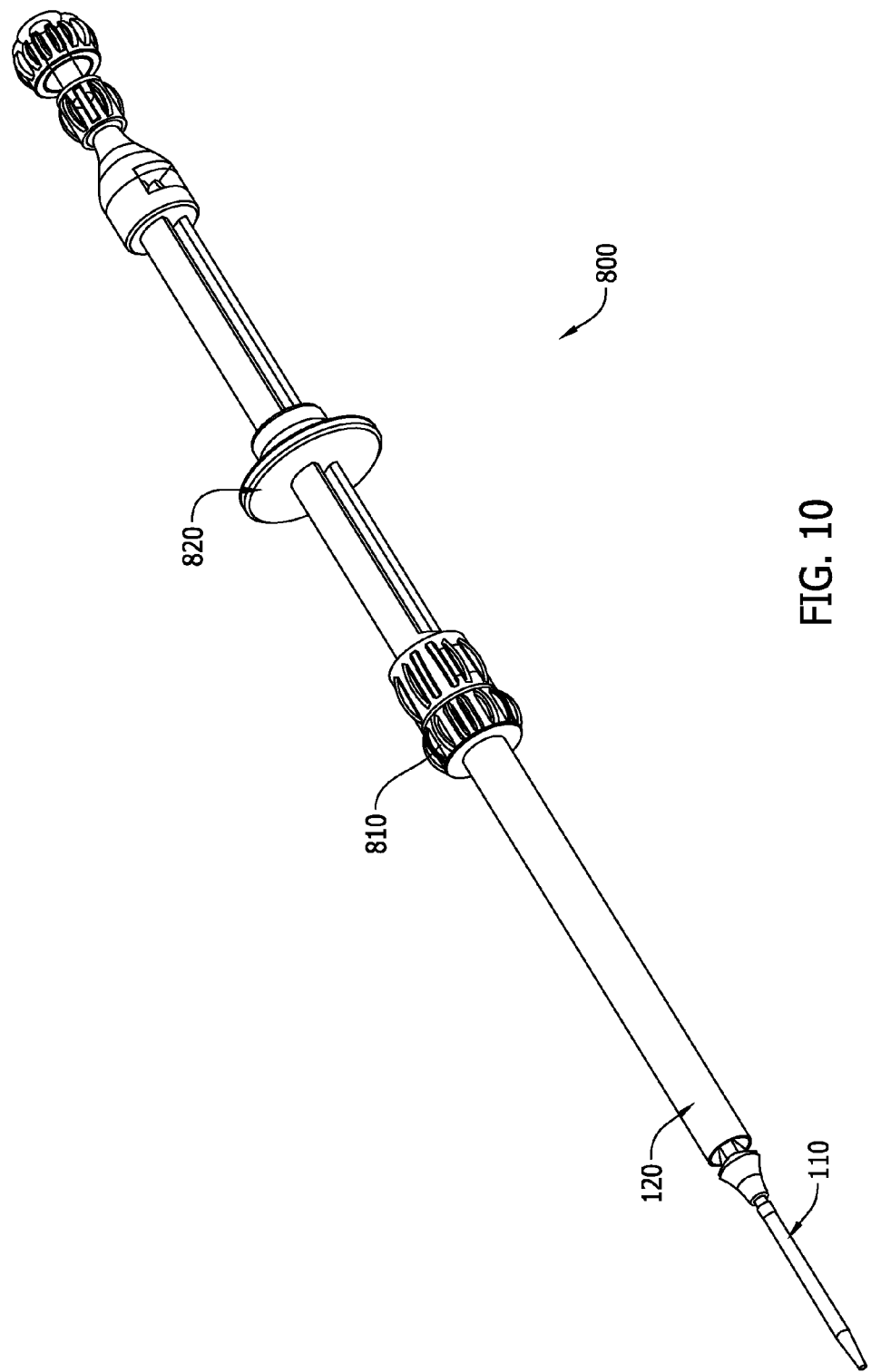
FIG. 10 is a perspective view of the hemostatic device shown in FIG. 9 in an open configuration.

FIG. 9 is a perspective view of another exemplary hemostatic device 800 for sealing a puncture of a vessel (not shown) in a closed configuration, and FIG. 10 is a perspective view of hemostatic device 800 in a deployed configuration. Hemostatic device 800 is similar to hemostatic device 100 and 700 and, in the absence of a contrary representation, the same reference numbers identify the same or similar elements.

In the exemplary embodiment, outer tube 120 is longitudinally movable with respect to inner tube 110, such that hemocoagulant agent 250 is at least substantially retained within outer lumen 240 when outer tube 120 is in the closed position (shown in FIG. 9), and is at least partially exposed to the environment when outer tube 120 is in the open position (shown in FIG. 10).

Figure 11:
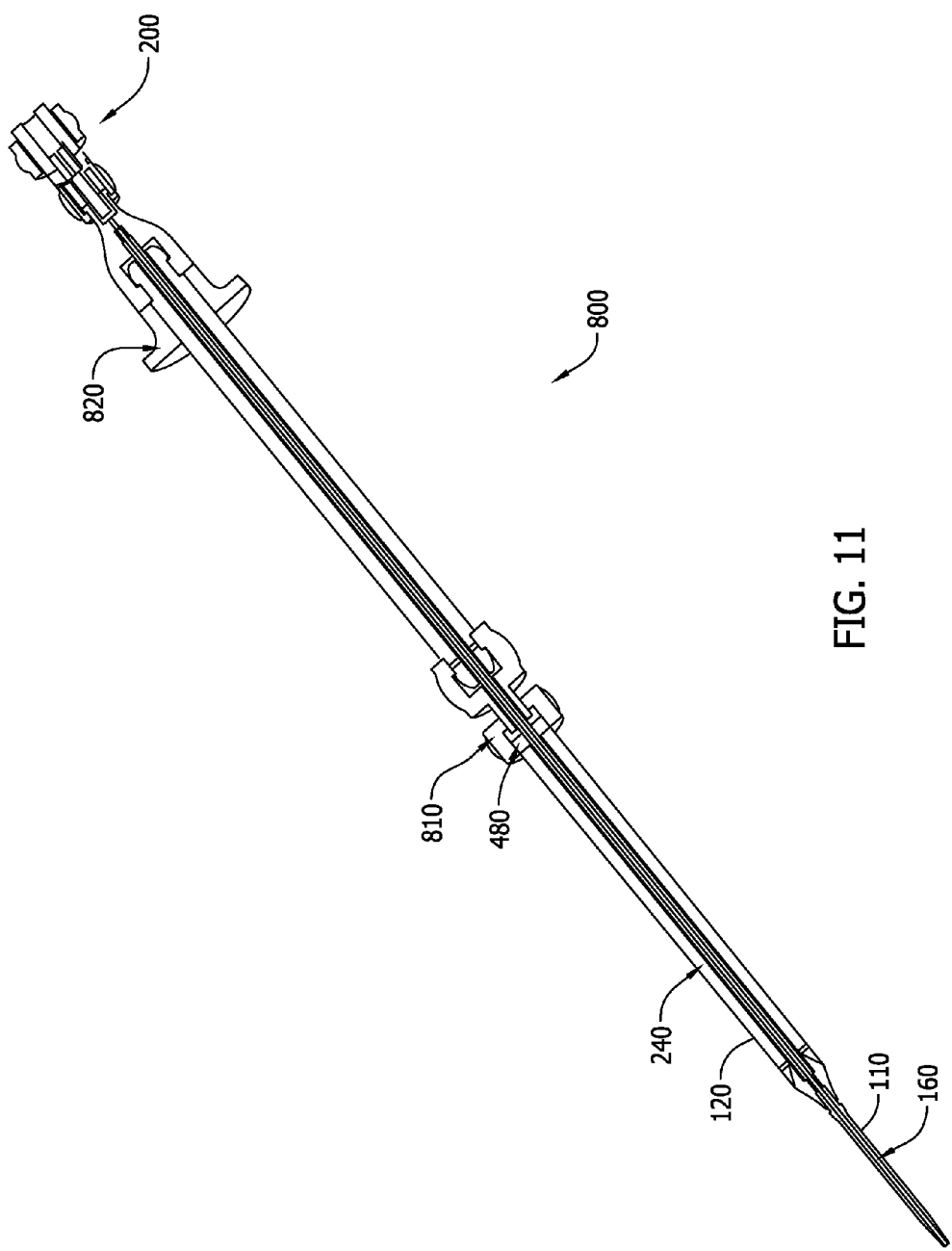
FIG. 11 is a cross-sectional view of the hemostatic device shown in FIG. 9.

FIG. 11 is a cross-sectional view of hemostatic device 800. In the exemplary embodiment, hemostatic device 800 includes an actuating mechanism 810 that facilitates moving outer tube 120 between the closed position and the open position. More specifically, actuating mechanism 810 is rotated in a first direction (e.g., a clockwise direction when looking from proximal end 140 towards distal end 130) to move outer tube 120 towards the closed position, and is rotated in a second direction (e.g., a counterclockwise direction when looking from proximal end 140 towards distal end 130) to move outer tube 120 towards the open position.

In the exemplary embodiment, plunger 480 is movable within outer lumen 240 to facilitate discharging hemocoagulant agent 250 from outer lumen 240. More specifically, plunger 480 is coupled to a handle 820 (shown in FIGS. 9 and 10) configured to move plunger 480 between a retracted or proximal position and a dispensing or distal position.

Figure 12:
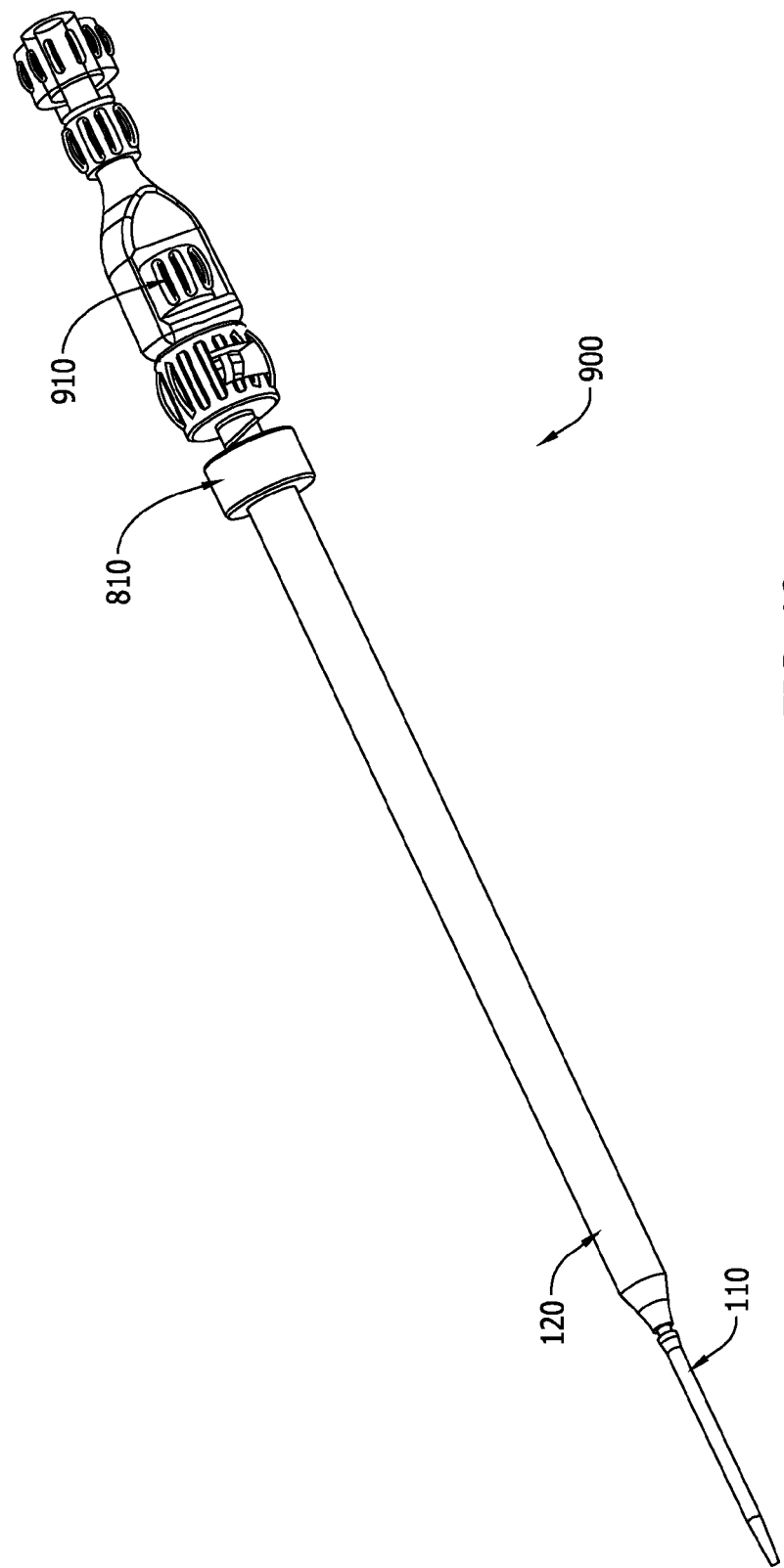
FIG. 12 is a perspective view of yet another exemplary hemostatic device.

FIG. 12 is a perspective view of another exemplary hemostatic device 900 for sealing a puncture of a vessel (not shown). Hemostatic device 900 is similar to hemostatic devices 100, 700, and 800 and, in the absence of a contrary representation, the same reference numbers identify the same or similar elements. In the exemplary embodiment, plunging mechanism 470 includes a wheel 910 configured to move plunger 480 between a retracted or proximal position and a dispensing or distal position.

Figure 13:
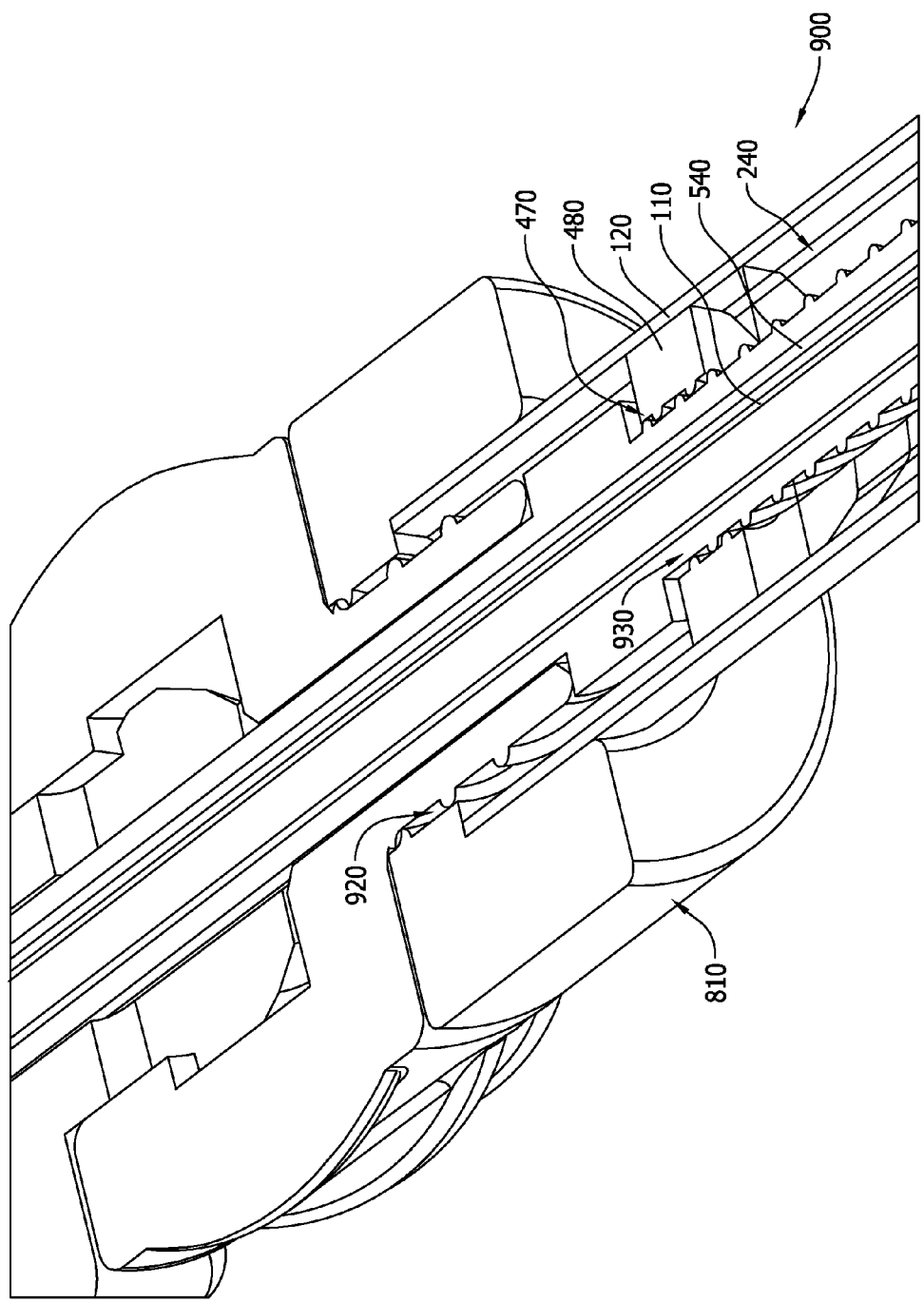
FIGS. 13 and 14 are cross-sectional views of a portion of the hemostatic device shown in FIG. 12.
Figure 14:
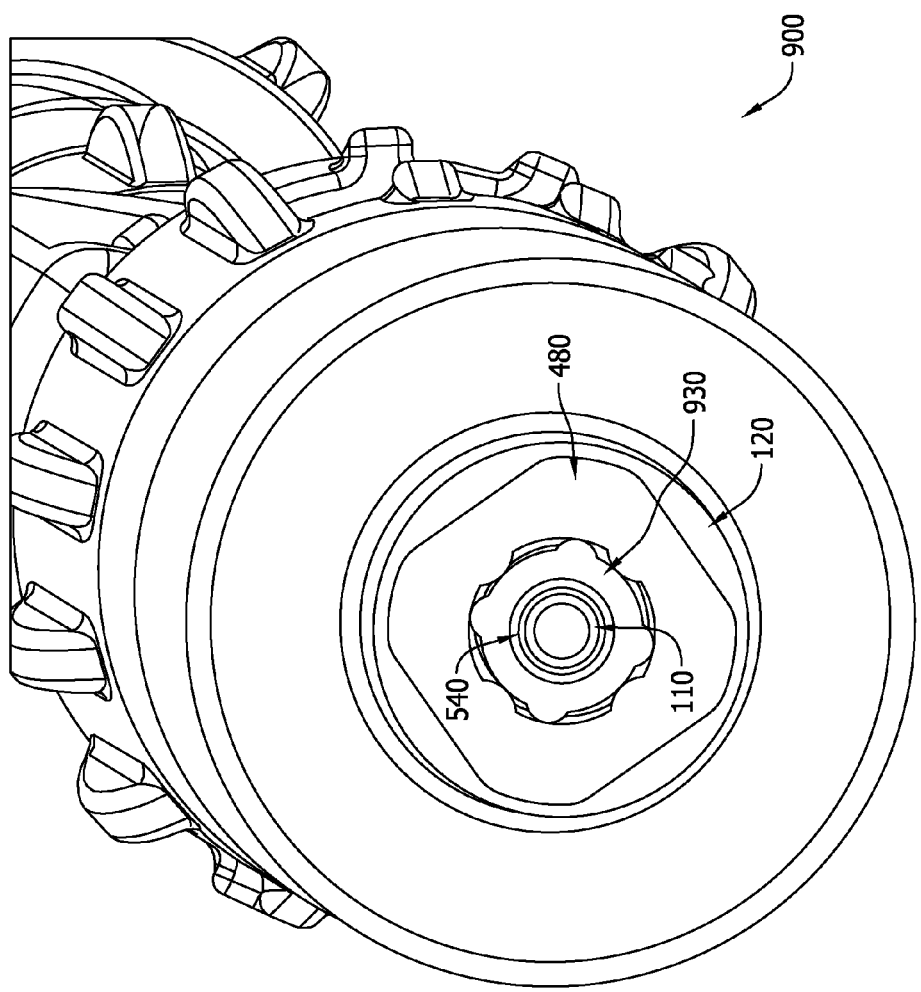

FIGS. 13 and 14 are cross-sectional views of a portion of hemostatic device 900. In the exemplary embodiment, actuating mechanism 810 includes a plurality of threads 920 that enables outer tube 120 to be moved between the closed position and the open position as actuating mechanism 810 is rotated.

In the exemplary embodiment, plunging mechanism 470 includes a plunger shaft 930 coupled to wheel 910, and plunger 480 is threadably coupled to plunger shaft 930. In the exemplary embodiment, an inner surface of outer tube 120 and/or an outer surface of plunger 480 is keyed or otherwise not round (e.g., substantially square-shaped) to prevent plunger 480 from rotating with respect to outer tube 120 as plunger shaft 930 is rotated, such that a rotation of wheel 910 and, thus, plunger shaft 930 longitudinally moves plunger 480 with respect to outer tube 120.

Figure 15:
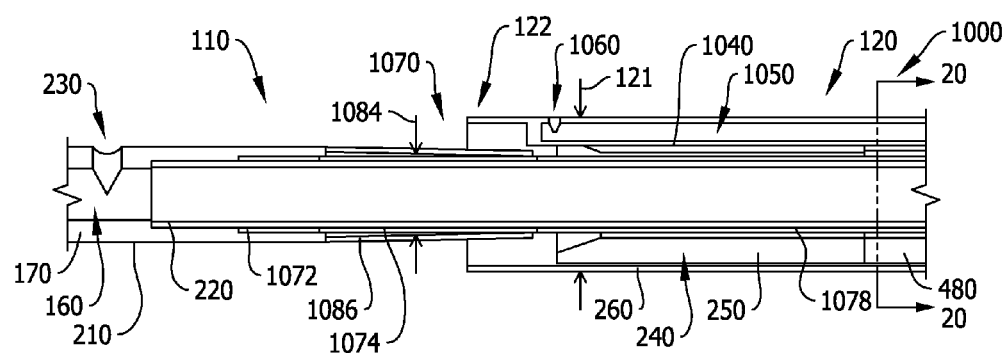
FIG. 15 is a cross-sectional view of yet another exemplary hemostatic device in a closed configuration and with an exemplary malecot in a retracted configuration.
Figure 16:
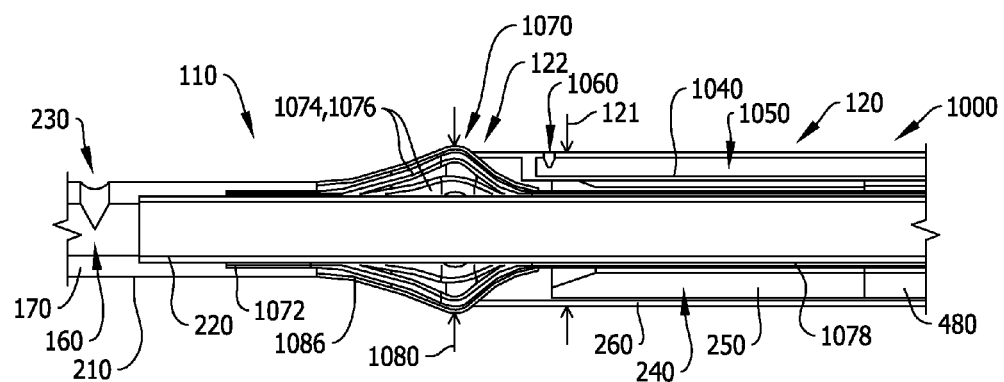
FIG. 16 is a cross-sectional view of the hemostatic device shown in FIG. 15 in the closed configuration with the exemplary malecot in a neutral configuration.
Figure 17:
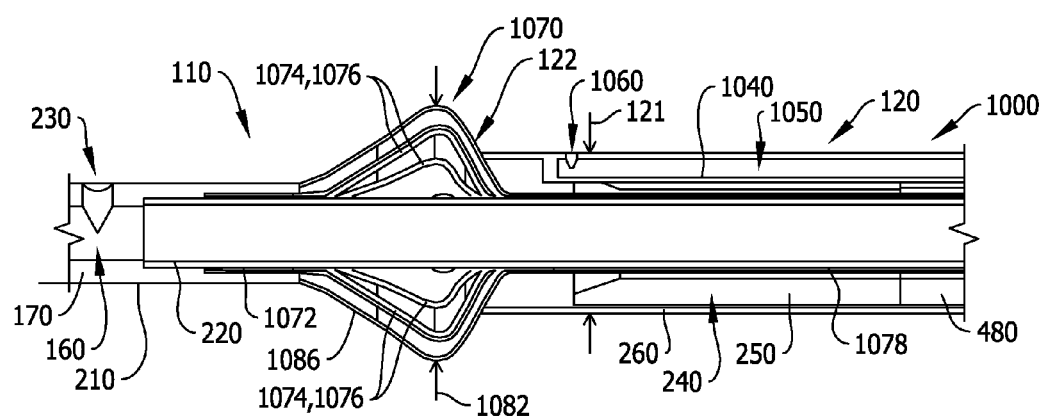
FIG. 17 is a cross-sectional view of the hemostatic device shown in FIG. 15 in the closed configuration with the exemplary malecot in a stopper configuration.
Figure 18:
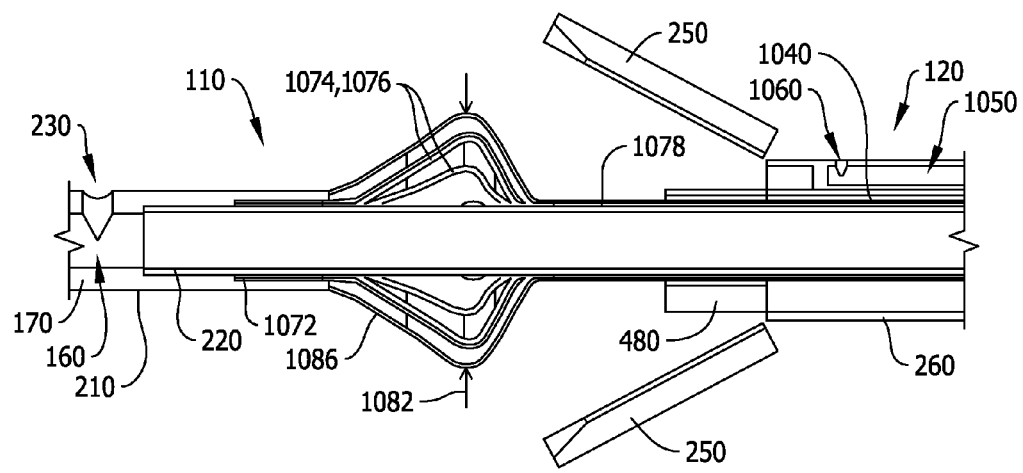
FIG. 18 is a cross-sectional view of the hemostatic device shown in FIG. 15 in a deployed configuration with the exemplary malecot in the stopper configuration.

FIGS. 15-17 are cross-sectional views of a portion of another exemplary hemostatic device 1000 for sealing a puncture of a vessel (not shown) in a closed configuration, and FIG. 18 is a cross-sectional view of hemostatic device 1000 in a deployed configuration. Hemostatic device 1000 is similar to hemostatic device 100, 700, 800, and 900 and, in the absence of a contrary representation, the same reference numbers identify the same or similar elements. In the exemplary embodiment, hemostatic device 1000 includes a malecot 1070 positioned with respect to outer tube 120, such that malecot 1070 is positionable within a lumen of a vessel and substantially adjacent a vessel access site when a distal end of outer tube 120 is outside and/or substantially adjacent a vessel access site.

Malecot 1070 includes a distal portion 1072 coupled to inner tube 110. In the exemplary embodiment, distal portion 1072 is rigidly coupled between distal portion 210 and proximal portion 220 of inner tube 110 by an interference fit. Alternatively, distal portion 1072 is coupled to at least one of distal portion 210 and proximal portion 220 in any configuration and/or using any mechanism that enables malecot 1070 to function as described herein.

In the exemplary embodiment, malecot 1070 also includes an expandable portion 1074 proximal to distal portion 1072. Expandable portion 1074 is disposed circumferentially about inner tube 110 proximal to inner tube side opening 230. In addition, at least a portion of expandable portion 1074 is disposed distal to outer tube 120. Malecot 1070, and specifically expandable portion 1074 of malecot 1070, is selectively actuatable between a neutral configuration (shown in FIG. 16) and a stopper configuration (shown in FIG. 17). In the neutral configuration, expandable portion 1074 has a first diameter 1080. In the stopper configuration, expandable portion 1074 has a second diameter 1082 that is greater than first diameter 1080, and greater than an outer diameter 121 of outer tube 120. Moreover, in the exemplary embodiment, malecot 1070 is configured such that second diameter 1082 is greater than a diameter of an opening in a vessel wall at a vessel access site, as will be described herein. Thus, malecot 1070 in the stopper configuration is configured to facilitate positioning outer tube distal end 122 outside the lumen of the vessel, and adjacent to the vessel wall, prior to the release of hemocoagulant agent 250 from hemostatic device 1000, and to substantially seal the vessel wall from penetration by hemocoagulant agent 250 at the access site, as will be described herein.

In the exemplary embodiment, malecot 1070 is further selectively actuatable between a retracted configuration (shown in FIG. 15) and each of the neutral configuration and the stopper configuration. In the retracted configuration, expandable portion 1074 has a third diameter 1084 that is less than first diameter 1080. In alternative embodiments, malecot 1070 is not selectively actuatable to the retracted configuration.

Malecot 1070 in the neutral configuration is configured to seal a distal end 122 of outer tube 120, such that hemocoagulant agent 250 is at least substantially sealed within outer lumen 240 when hemostatic device 1000 is in a closed configuration. For example, in the exemplary embodiment, when malecot 1070 is in the neutral configuration, outer tube distal end 122 is configured to circumscribe a proximal portion of expandable portion 1074 in substantially sealing contact, such that hemocoagulant agent 250 is substantially sealed from exposure to blood until hemostatic device 1000 is moved to the deployed configuration. Also in the exemplary embodiment, first diameter 1080 is less than or approximately equal to outer tube outer diameter 121 to facilitate traversing hemostatic device 1000 through subcutaneous tissue. In alternative embodiments, first diameter 1080 is greater than outer tube outer diameter 121.

Figure 19:
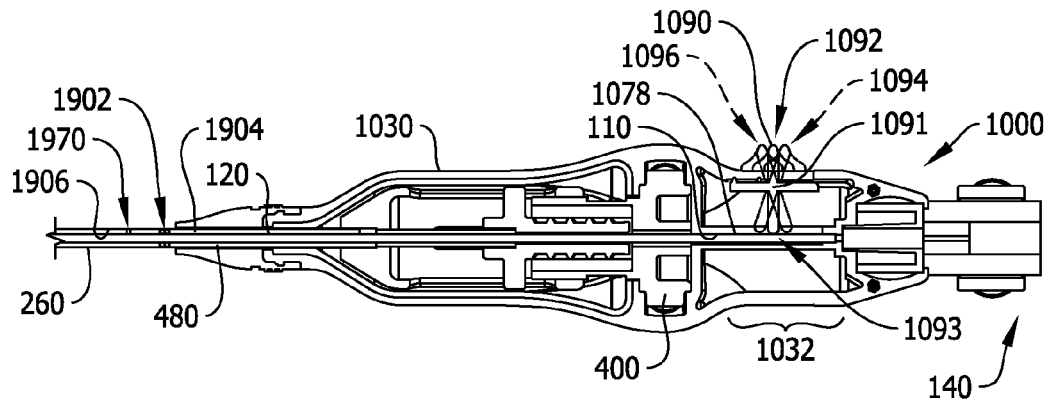
FIG. 19 is a cross-sectional view of an exemplary housing of the hemostatic device shown in FIG. 15.

FIG. 19 is a cross-sectional view of an exemplary housing 1030 of hemostatic device 1000. Housing 1030 is similar to housing 330 and, in the absence of a contrary representation, the same reference numbers identify the same or similar elements. In the exemplary embodiment, however, housing 1030 includes an elongated portion 1032 disposed proximal to wheel 400. In alternative embodiments, elongated portion 1032 is disposed at another longitudinal location along housing 1030. In other alternative embodiments, housing 1030 does not include elongated portion 1032.

With reference to FIGS. 15-19, in certain embodiments, hemostatic device 1000 includes a plug actuator 1090 coupled to malecot 1070. In the exemplary embodiment, plug actuator 1090 also is coupled to elongated portion 1032 of housing 1030. In alternative embodiments, plug actuator is coupled to any suitable portion of housing 1030 that enables plug actuator 1090 to function as described herein. Plug actuator 1090 is configured to selectively actuate malecot 1070 between at least the neutral configuration (shown in FIG. 16) and the stopper configuration (shown in FIG. 17). In some embodiments, plug actuator 1090 is further configured to selectively actuate malecot 1070 between the retracted configuration (shown in FIG. 15) and the neutral configuration and stopper configuration.

For example, in the exemplary embodiment, each of plug actuator 1090 and malecot 1070 is operably coupled to a transfer member 1078. Transfer member 1078 extends longitudinally between plug actuator 1090 and malecot 1070, and is selectively operable by plug actuator 1090 for longitudinal translation with respect to inner tube 110. In the exemplary embodiment, transfer member 1078 is a tube disposed coaxially with, and radially outwardly from, inner tube 110. In alternative embodiments, transfer member 1078 has any suitable structure that enables malecot 1070 to function as described herein.

For example, in the exemplary embodiment, plug actuator 1090 is pivotally coupled to housing 1030 at a pivot 1091, and a radially inner end 1093 of plug actuator 1090 is coupled to transfer member 1078 such that pivotal movement of plug actuator 1090 results in longitudinal translational motion of transfer member 1078. For example, but not by way of limitation, radially inner end 1093 includes a slot (not shown) that cooperates with oppositely disposed, transversely extending pegs (not shown) on transfer member 1078. Alternatively, plug actuator 1090 and transfer member 1078 each include any suitable structure such that pivotal movement of plug actuator 1090 results in longitudinal translational motion of transfer member 1078.

In some embodiments, expandable portion 1074 includes a plurality of reversibly deformable segments 1076. For example, in the exemplary embodiment, deformable segments 1076 are arranged circumferentially around inner tube 110, and each deformable segment 1076 extends longitudinally over a portion of inner tube 110. More specifically, deformable segments 1076 extend longitudinally between malecot distal portion 1072, which is rigidly coupled to inner tube 110, and a distal end of transfer member 1078. Deformable segments 1076 are configured to reversibly deform radially outward from inner tube proximal portion 220 to accommodate longitudinal translation of transfer member 1078 towards fixed malecot distal portion 1072, and to reversibly deform radially inward towards inner tube proximal portion 220 to accommodate longitudinal translation of transfer member 1078 away from fixed malecot distal portion 1072. Thus, deformable segments 1076 selectively define each of first diameter 1080, second diameter 1082, and third diameter 1084 of expandable portion 1074 in response to a respective corresponding longitudinal position of transfer member 1078 relative to inner tube 110.

In the exemplary embodiment, plug actuator 1090 is selectively movable between a first position 1092, a second position 1094 (shown in phantom lines in FIG. 19), and a third position 1096 (shown in phantom lines in FIG. 19). In first position 1092, transfer member 1078 is longitudinally positioned with respect to inner tube 110 such that deformable segments 1076 radially deform to transition malecot 1070 to the neutral configuration (shown in FIG. 16). In second position 1094, transfer member 1078 is longitudinally positioned with respect to inner tube 110 such that deformable segments 1076 radially deform to transition malecot 1070 to the stopper configuration (shown in FIG. 17). In third position 1096, transfer member 1078 is longitudinally positioned with respect to inner tube 110 such that deformable segments 1076 radially deform to transition malecot 1070 to the retracted position (shown in FIG. 15). In alternative embodiments, plug actuator 1090 is selectively movable between first position 1092 and second position 1094, but not to third position 1096.

In certain embodiments, transfer member 1078, malecot distal portion 1072, and expandable portion 1074 are formed unitarily from a single tube. For example, the single tube has a length equal to a combined length of transfer member 1078, expandable portion 1074 in the retracted configuration, and distal portion 1072. Deformable segments 1076 are defined on expandable portion 1074 by a plurality of circumferentially disposed, longitudinally extending slots. More specifically, each slot extends radially through a sidewall of the tube along expandable portion 1074, such that each slot separates a pair of adjacent deformable segments 1076. In alternative embodiments, each of transfer member 1078, malecot distal portion 1072, and expandable portion 1074 are fabricated from any suitable number of components coupled together in any suitable fashion that enables malecot 1070 to function as described herein.

In the exemplary embodiment, expandable portion 1074 is formed from a material that provides a desired degree of deformability to deformable segments 1076. For example, but not by way of limitation, expandable portion 1074 is fabricated from a Nitinol alloy. In some embodiments, transfer member 1078 and malecot distal portion 1072 also are formed from a Nitinol alloy. In alternative embodiments, each of transfer member 1078, malecot distal portion 1072, and expandable portion 1074 is fabricated from any suitable material that enables malecot 1070 to function as described herein.

In the exemplary embodiment, a flexible sleeve 1086 is disposed circumferentially around expandable portion 1074 to facilitate preventing interaction between deformable segments 1076 and subcutaneous tissue. For example, but not by way of limitation, sleeve 1086 is formed from an elastomer material. In alternative embodiments, hemostatic device 1000 does not include sleeve 1086.

Additionally, in the exemplary embodiment, outer tube 120 of hemostatic device 1000 includes a proximal portion 1904 and a distal portion 1906 releasably coupled together by an interlock mechanism 1902. Interlock mechanism 1902 is configured to couple proximal portion 1904 and distal portion 1906 in flow communication, such that outer tube lumen 240 is defined in, and extends continuously through, each of proximal portion 1904 and distal portion 1906. Interlock mechanism 1902 also is configured to selectively uncouple proximal portion 1904 and distal portion 1906, such that hemostatic device 1000 and outer tube proximal portion 1904 may be withdrawn and removed from subcutaneous tissue while outer tube distal portion 1906 remains positioned within the subcutaneous tissue, for example after hemostatic device 1000 is oriented to the deployed configuration and hemocoagulant agent 250 is released. Interlock mechanism 1902 is any suitable mechanism that enables proximal portion 1904 and distal portion 1906 of outer tube 120 to be selectively uncoupled as described herein.

Figure 20:
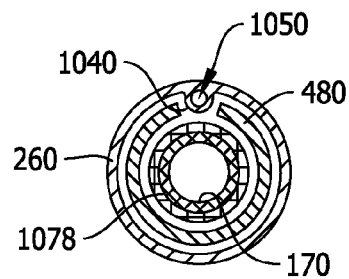
FIG. 20 is a cross-sectional view of the hemostatic device shown in FIG. 15 taken along lines 20-20 shown in FIG. 15.

FIG. 20 is a cross-sectional view of hemostatic device 1000 taken along lines 20-20 shown in FIG. 15. With reference to FIGS. 15 and 20, in the exemplary embodiment, hemostatic device 1000 includes a third or intermediate tube 1040 positioned radially between inner tube 110 and outer tube 120. More specifically, intermediate tube 1040 is positioned such that a third or intermediate lumen 1050 configured to channel blood or, more broadly, a fluid therethrough is at least partially defined by intermediate tube 1040. In the exemplary embodiment, intermediate lumen 1050 is in fluid communication with a first opening 1060 extending through outer tube 120. In certain embodiments, intermediate lumen 1050 also is in fluid communication with second opening 570 (shown in FIG. 1) extending through housing 330, such that fluid may enter intermediate lumen 1050 through first opening 1060 and is dischargeable through second opening 570. In alternative embodiments, intermediate lumen 1050 is in fluid communication with an alternative second opening 1970 (shown in FIG. 19) that extends through sidewall 260 of outer tube 120, distal to interlock mechanism 1902, such that fluid may enter intermediate lumen 1050 through first opening 1060 and is dischargeable through alternative second opening 1970.

In certain embodiments, a reflux of blood from a lumen of a vessel through outer tube first opening 1060, intermediate lumen 1050, and one of housing opening 570 and alternative second opening 1970 provides sufficient visual information regarding a position of malecot 1070 as will be described herein, such that inner tube 110 need not include inner tube side opening 230, and inner tube lumen 160 is sized to accommodate a guidewire (not shown) in a clearance fit from first end 130 to second end 140, rather than to additionally channel a reflux of blood. In alternative embodiments, hemostatic device 1000 includes inner tube side opening 230, inner tube lumen 160 sized to accommodate a reflux of blood, third tube 540, and third lumen 550 as shown in FIG. 3. In other alternative embodiments, hemostatic device 1000 includes inner tube side opening 230 and inner tube lumen 160 sized to accommodate a reflux of blood, and does not include any third tube and/or third lumen.

Figure 21:
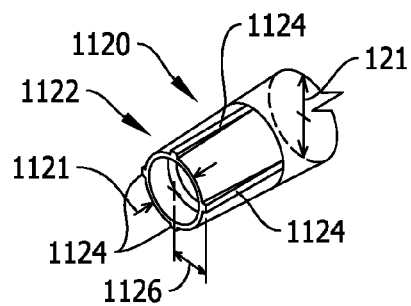
FIG. 21 is a perspective view of a distal portion of an exemplary outer tube that may be used with the hemostatic device shown in FIG. 15.

FIG. 21 is a perspective view of a distal portion 1122 of an exemplary outer tube 1120 that may be used with hemostatic device 1000. Outer tube 1120 is similar to outer tube 120 and, in the absence of a contrary representation, the same reference numbers identify the same or similar elements. In the exemplary embodiment, distal portion 1122 is substantially tapered, such that an outer diameter 1121 of outer tube 1120 decreases along distal portion 1122. Tapered distal portion 1122 is configured to facilitate traversing outer tube 1120 through subcutaneous tissue.

Additionally in the exemplary embodiment, an outer surface of distal portion 1122 includes a plurality of longitudinally extending ridges 1124 spaced circumferentially about distal portion 1122. In the exemplary embodiment, ridges 1124 are configured such that twice a radial distance 1126 from a centerline of outer tube 1120 to an outer surface of ridge 1124 is approximately equal to outer diameter 121 of outer tube 1120 proximal to distal portion 1122. Ridges 1124 are configured to provide a tactile indication (e.g., resistance) that outer tube distal end 1122 has encountered and/or is passing through a wall of the vessel.

Figure 22:
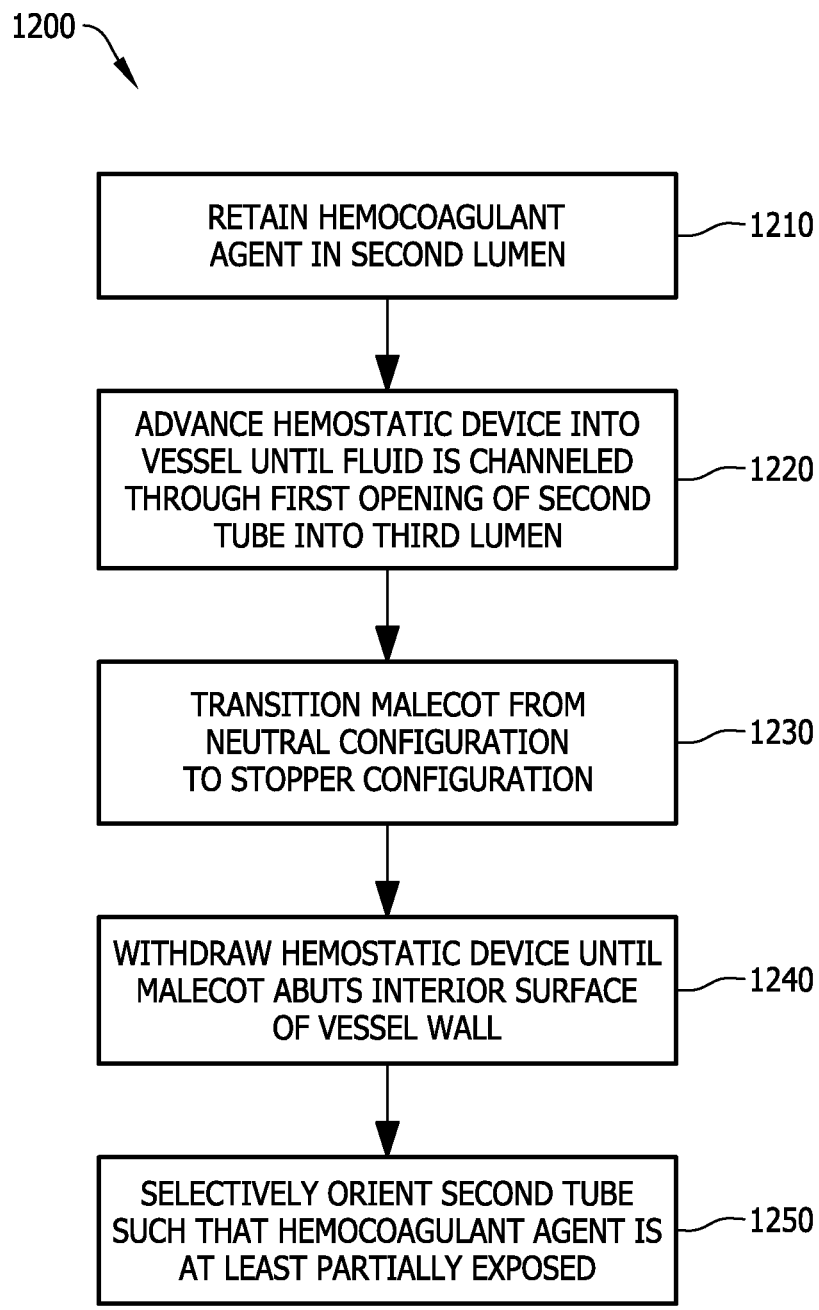
FIG. 22 is a flow chart illustrating an exemplary method of using the hemostatic device shown in FIG. 15.

FIG. 22 is a flow chart illustrating an exemplary method 1200 of using hemostatic device 1000 to seal a puncture opening 2306 in an artery or vessel 2300 with a hydrogel polymer or collagen patch hemocoagulant agent 250. FIGS. 23-28 illustrate hemostatic device 1000 during various stages of method 1200. In at least some implementations, hemocoagulant agent 250 is preloaded into hemostatic device 1000, such that hemocoagulant agent 250 is retained 1210 within outer lumen 240. Alternatively, hemocoagulant agent 250 is loaded into hemostatic device 1000, such that hemocoagulant agent is retained 1210 within outer lumen 240, by selectively rotating wheel 400 (shown in FIGS. 4-6) and/or substantially enveloping or circumscribing hemocoagulant agent 250 about inner tube 110. In the exemplary implementation, malecot 1070 is positioned in the neutral configuration (shown in FIG. 16) with respect to outer tube 120 or outer tube 1120. For example, malecot 1070 is positioned in the neutral configuration to facilitate retaining 1210 hemocoagulant agent 250 within outer lumen 240.

Figures 23, 24:
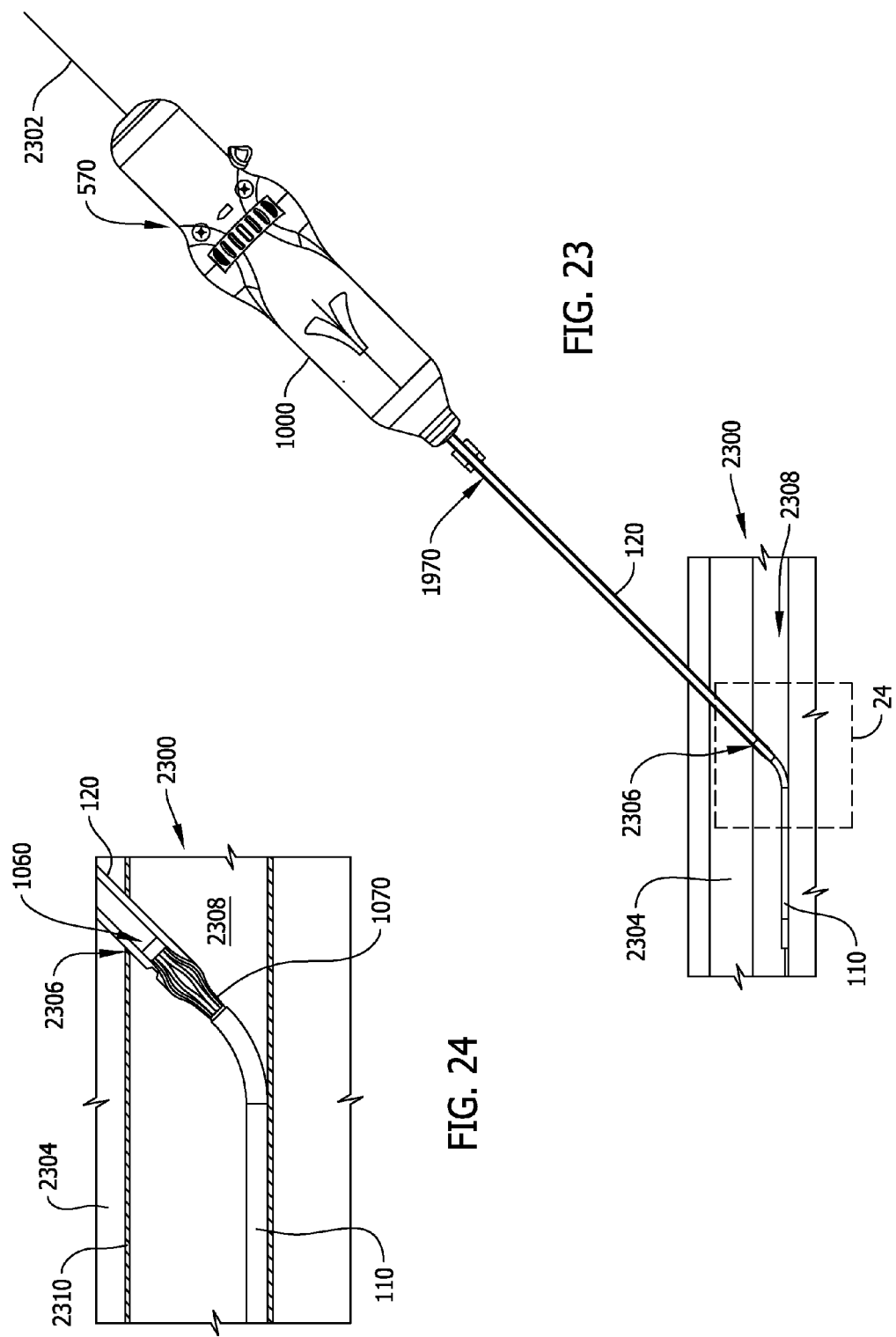
FIG. 23 is a schematic view of the hemostatic device shown in FIG. 15 in the closed configuration and positioned within a blood vessel, with the exemplary malecot in the neutral configuration shown in FIG. 16.
FIG. 24 is a detail of the schematic view shown in FIG. 23.

During operation, inner tube 110 is aligned such that a guidewire 2302 extends through first opening 180 and second opening 190, and malecot 1070 is in the neutral position. Hemostatic device 1000 is advanced 1220 along guidewire 2302 through subcutaneous tissue 2304 into lumen 2308 of vessel 2300 until blood is channeled through outer tube first opening 1060 and intermediate lumen 1050 and discharged from one of housing second opening 570 and alternative second opening 1970. In the exemplary embodiment, the blood discharge (i.e., reflux) from one of housing second opening 570 and alternative second opening 1970 is a visual indication that outer tube first opening 1060 is positioned within the vessel, as shown in FIGS. 23 and 24. In at least some implementations, at least one of malecot 1070 and longitudinal ridges 1124 provides a tactile indication (e.g., resistance from a wall 2310 of vessel 2300 surrounding puncture opening 2306) that outer tube distal portion 122 or 1122 has passed through the vessel wall. Additionally or alternatively, in at least certain implementations, hemostatic device 1000 includes inner tube side opening 230, and a blood discharge (i.e., reflux) from inner tube second opening 190 is a visual indication that inner tube side opening 230 is positioned within the vessel.

Figure 25:
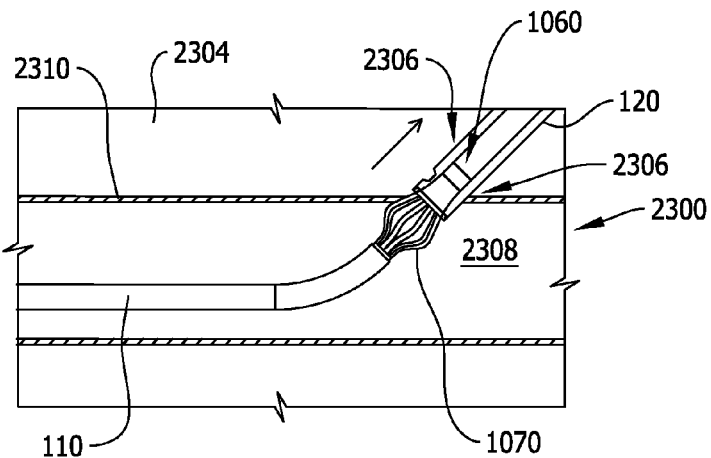
FIG. 25 is a schematic view of the hemostatic device shown in FIG. 15 in the closed configuration and positioned within a blood vessel, with the exemplary malecot in the stopper configuration shown in FIG. 17.

In the exemplary embodiment, plug actuator 1090 is selectively moved to second position 1094 such that malecot 1070 is transitioned 1230 from the neutral configuration to the stopper configuration. Malecot 1070 in the stopper configuration has second diameter 1082 that is greater than a diameter of opening 2306 in vessel wall 2310, which inhibits malecot 1070 from passing back through vessel wall 2310 and out of vessel lumen 2308. Hemostatic device 1000 is then withdrawn 1240 along guidewire 2302 until resistance is met, indicating that malecot 1070 is abutting an interior surface of vessel wall 2310 and, therefore, that outer tube distal end 122 or 1122 has moved from inside vessel lumen 2308 to outside, and adjacent to, vessel wall 2310, as shown in FIG. 25. In at least some implementations, the position of outer tube distal end 122 or 1122 outside vessel lumen 2308 is confirmed by an absence or substantial reduction of blood discharge from one of housing second opening 570 and alternative second opening 1970. Malecot 1070 abutting the interior surface of vessel wall 2310 facilitates ensuring that hemocoagulant agent 250 will be released outside vessel lumen 2308 and facilitates occluding puncture opening 2306, such that hemocoagulant agent 250, once released, does not enter vessel lumen 2308.

Figure 26:
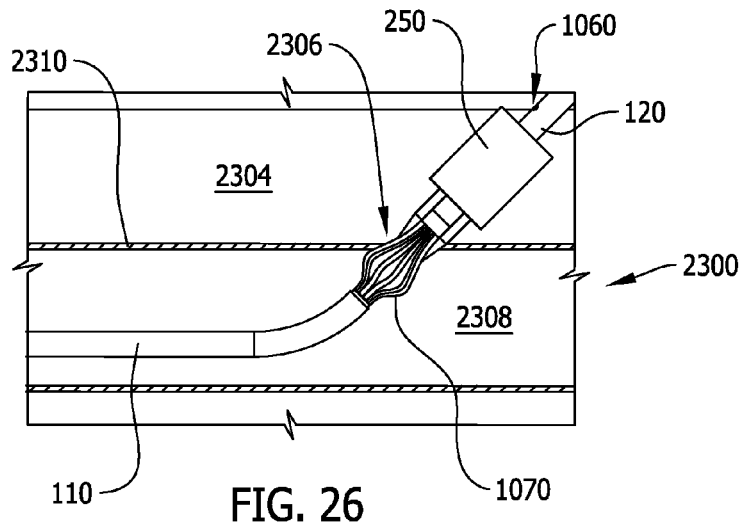
FIG. 26 is a schematic view of the hemostatic device shown in FIG. 15 in the deployed configuration shown in FIG. 18 and positioned within a blood vessel, with the exemplary malecot in the stopper configuration shown in FIG. 17.

Further in the exemplary embodiment, outer tube 120 or 1120 is selectively oriented 1250 such that hemocoagulant agent 250 is at least partially exposed, as shown in FIG. 26. For example, wheel 400 is selectively rotated in the second direction to move hemostatic device 1000 towards the deployed configuration and, thus, orient 1250 outer tube 120 or outer tube 1120 towards the deployed position (shown in FIG. 18). Accordingly, hemocoagulant agent 250 is at least partially exposed to the environment. As wheel 400 is selectively rotated in the second direction, plunger carrier 490 (shown in FIGS. 5 and 6) and, thus, plunger 480 is moved in the distal direction, such that hemocoagulant agent 250 is pushed at least partially in the distal direction towards outer tube distal portion 122 or 1122. In at least some implementations, outer tube 120 or outer tube 1120 is oriented 1240 towards the deployed position and plunger 480 is moved towards the distal direction simultaneously. In at least some implementations, a withdrawal force is maintained on hemostatic device 1000 such that malecot 1070 in the stopper configuration is maintained in abutment against the interior surface of vessel wall 2310.

Figure 27:
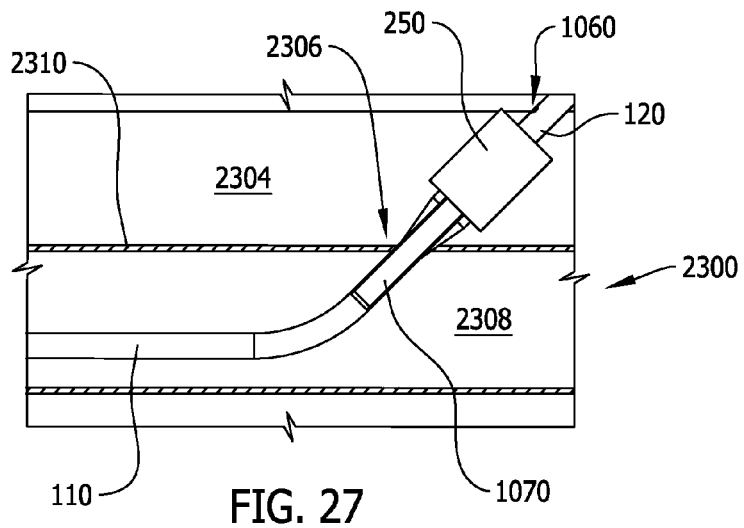
FIG. 27 is a schematic view of the hemostatic device shown in FIG. 15 in the deployed configuration shown in FIG. 18 and positioned within a blood vessel, with the exemplary malecot in the retracted configuration shown in FIG. 15.

In at least some implementations, plug actuator 1090 is selectively moved to third position 1096 such that malecot 1070 is transitioned to the retracted configuration, as shown in FIG. 27, to facilitate withdrawal of hemostatic device 1000 from the subcutaneous tissue, leaving hemocoagulant agent 250 proximate an exterior surface of vessel wall 2310. In some other implementations, plug actuator 1090 is selectively moved to first position 1092 such that malecot 1070 is transitioned to the neutral configuration to facilitate withdrawal of hemostatic device 1000 from the subcutaneous tissue, leaving hemocoagulant agent 250 proximate an exterior surface of vessel wall 2310.

Figure 28:
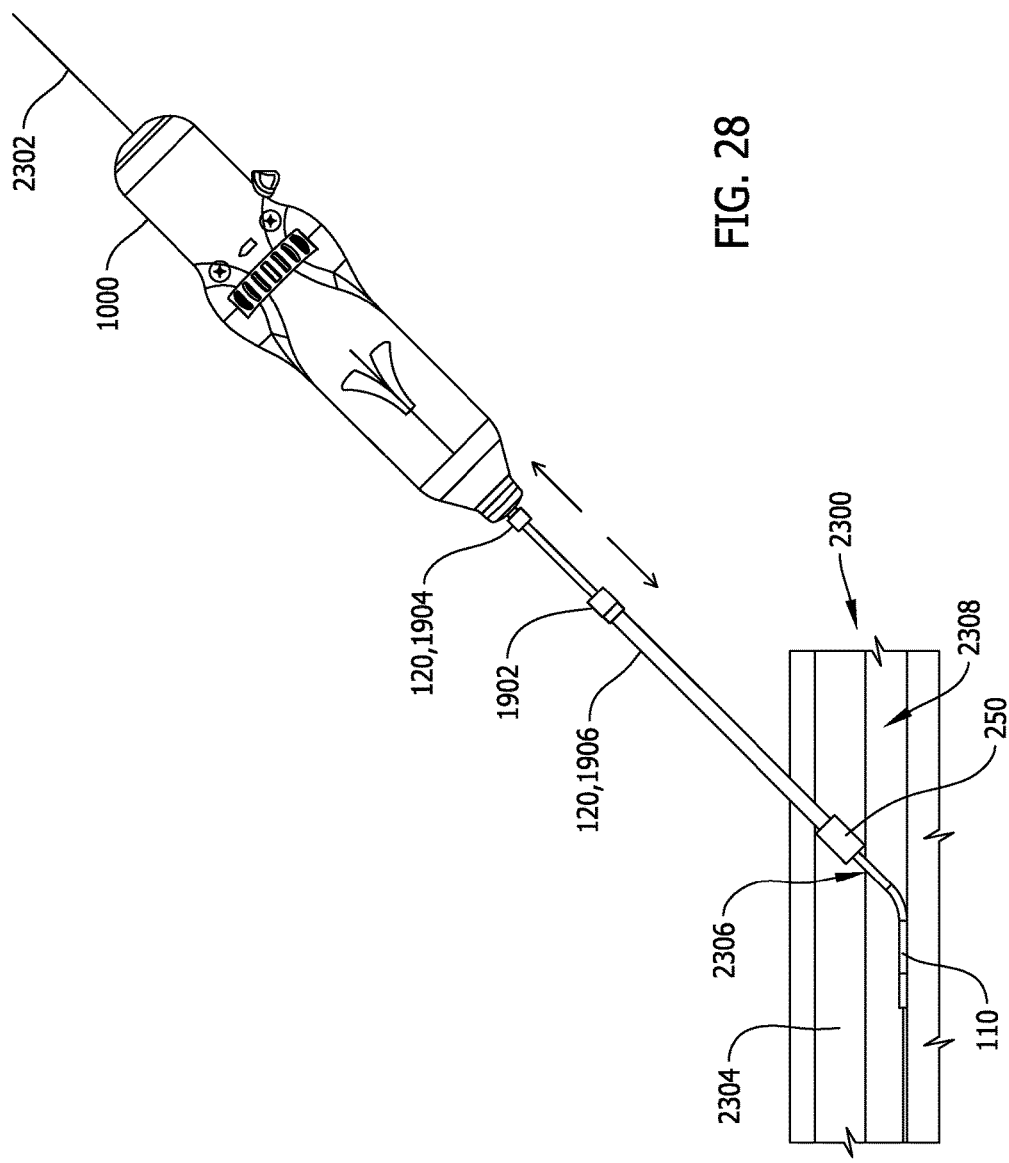
FIG. 28 is a schematic view of the hemostatic device shown in FIG. 15 with an exemplary interlock mechanism uncoupled.

In at least some implementations, proximal portion 1904 and distal portion 1906 of outer tube 120 are uncoupled, as shown in FIG. 28, such as by selectively activating interlock mechanism 1902. Forward pressure is applied to uncoupled distal portion 1906 to facilitate maintaining hemocoagulant agent 250 proximate the exterior surface of vessel wall 2310, while inner tube 110 and proximal portion 1904 are concurrently withdrawn from vessel 2300 and subcutaneous tissue 2304. Finally, distal portion 1906 is withdrawn from subcutaneous tissue 2304 and pressure is applied over puncture opening 2306 until homeostasis is achieved.

The methods and apparatus described herein relate to medical devices and, more particularly, to a hemostatic device. The methods and apparatus described herein facilitate sealing, for example, an arterial opening. The exemplary hemostatic device includes a first tube defining a first lumen, a second tube circumscribing at least a portion of the first tube and at least partially defining a second lumen configured to retain a hemocoagulant agent therein, and a malecot that is selectively actuatable between a neutral configuration and a stopper configuration. The malecot is transitioned to the stopper configuration and the second tube is oriented to expose at least some of the hemocoagulant agent to the environment, while a plunger is moved through the second lumen to facilitate discharging the hemocoagulant agent. The hemocoagulant agent facilitates sealing the arterial opening to reduce a time required for hemostasis and/or ambulation.

Exemplary embodiments of medical devices are described above in detail. The methods and systems are not limited to the specific embodiments described herein, but rather, operations of the methods and components of the systems may be utilized independently and separately from other operations and/or components described herein. For example, the methods and apparatus described herein may have other industrial and/or consumer applications and are not limited to practice with medical devices as described herein. Rather, one or more embodiments may be implemented and utilized in connection with other industries.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A hemostatic device for sealing a puncture of a vessel, said hemostatic device comprising:
   a first tube defining a first lumen;
   a malecot coupled to the first tube, the malecot selectively actuatable from a neutral configuration to a stopper configuration;
   a housing;
   a plug actuator coupled to the housing, the plug actuator operable to selectively transition the malecot between the neutral configuration and the stopper configuration;
   a transfer member coupled to the malecot, the transfer member longitudinally positionable with respect to the first tube to transition the malecot from the neutral configuration to the stopper configuration, wherein the transfer member comprises a tube disposed coaxially with, and radially outwardly from, the first tube; and
   a second tube circumscribing at least a portion of the first tube and at least partially defining a second lumen and a third lumen, the second tube comprising a first opening in flow communication with the third lumen and positioned proximally relative to the malecot, the third lumen extending from the first opening proximally through the second tube to a second opening in flow communication with an exterior of the hemostatic device, the second tube selectively orientable to at least partially expose a hemocoagulant agent retained in the second lumen.

2. A hemostatic device in accordance with claim 1, wherein the transfer member is selectively operable for longitudinal translation with respect to the first tube by a plug actuator coupled to a housing of the hemostatic device.

3. A hemostatic device in accordance with claim 1, wherein the malecot comprises a plurality of deformable segments, the transfer member configured to reversibly deform the plurality of deformable segments radially outward from the first tube to transition the malecot from the neutral configuration to the stopper configuration.

4. A hemostatic device in accordance with claim 3, wherein the malecot further comprises a distal portion rigidly coupled to the first tube, the plurality of deformable segments is disposed between the malecot distal portion and the transfer member.

5. A hemostatic device in accordance with claim 4, wherein the transfer member, the malecot distal portion, and the plurality of deformable segments are formed unitarily from a single tube.

6. A hemostatic device in accordance with claim 1, wherein the second tube further comprises a proximal portion releasably coupled to a distal portion.

7. A hemostatic device for sealing a puncture of a vessel, said hemostatic device comprising:
   a housing;
   a first tube defining a first lumen;
   a malecot coupled to the first tube;

a plug actuator coupled to the housing, the plug actuator operable to selectively transition the malecot between a neutral configuration and a stopper configuration;

a transfer member selectively operable by the plug actuator for longitudinal translation with respect to the first tube to transition the malecot from the neutral configuration to the stopper configuration;

a second tube circumscribing at least a portion of the first tube and at least partially defining a second lumen and a third lumen, the second tube comprising a first opening in flow communication with the third lumen and positioned proximally relative to the malecot, the third lumen extending from the first opening proximally through the second tube to a second opening in flow communication with an exterior of the hemostatic device, the second tube selectively orientable to at least partially expose a hemocoagulant agent retained in the second lumen;

wherein the transfer member comprises a third tube disposed coaxially with, and radially outwardly from, the first tube.

8. A hemostatic device in accordance with claim 7, wherein the malecot comprises a plurality of deformable segments, the transfer member configured to reversibly deform the plurality of deformable segments radially outward from the first tube to transition the malecot from the neutral configuration to the stopper configuration.

\* \* \* \* \*